US006875886B2

(12) United States Patent
Frangioni

(10) Patent No.: US 6,875,886 B2
(45) Date of Patent: Apr. 5, 2005

(54) MODIFIED PSMA LIGANDS AND USES RELATED THERETO

(75) Inventor: John V. Frangioni, Wayland, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 169 days.

(21) Appl. No.: 10/071,890

(22) Filed: Feb. 7, 2002

(65) Prior Publication Data

US 2004/0110723 A1 Jun. 10, 2004

Related U.S. Application Data

(60) Provisional application No. 60/267,055, filed on Feb. 7, 2001.

(51) Int. Cl.[7] .............................................. C07C 229/00

(52) U.S. Cl. ........................ 560/171; 514/120; 514/121

(58) Field of Search .......................... 560/171; 514/121, 514/120

(56) References Cited

U.S. PATENT DOCUMENTS

| | | | | |
|---|---|---|---|---|
| 5,538,866 A | | 7/1996 | Israeli et al. | |
| 5,804,602 A | * | 9/1998 | Slusher et al. | 514/574 |
| 5,981,209 A | | 11/1999 | Slusher et al. | |
| 6,025,344 A | | 2/2000 | Jackson et al. | |
| 6,025,345 A | | 2/2000 | Jackson et al. | |
| 6,071,965 A | * | 6/2000 | Jackson et al. | 514/574 |
| 6,271,245 B1 | | 8/2001 | Jackson et al. | |
| 6,288,046 B1 | | 9/2001 | Jackson et al. | |
| 6,348,464 B1 | | 2/2002 | Jackson et al. | |
| 6,372,726 B1 | | 4/2002 | Slusher et al. | |
| 6,384,022 B1 | * | 5/2002 | Jackson et al. | 514/121 |
| 6,444,657 B1 | * | 9/2002 | Slusher et al. | 514/120 |
| 6,452,044 B2 | | 9/2002 | Jackson et al. | |

FOREIGN PATENT DOCUMENTS

| | | | |
|---|---|---|---|
| WO | WO 97/48399 | | 12/1997 |
| WO | WO 97/48400 | | 12/1997 |
| WO | WO 98/13046 | | 4/1998 |
| WO | WO 98/130046 | * | 4/1998 |
| WO | WO 98/45257 | | 10/1998 |
| WO | WO 99/32887 | | 7/1999 |
| WO | WO 02/057222 | | 7/2002 |

OTHER PUBLICATIONS

Valiaeva et al J. Organic Chemistry, 2001, vol. 66 pp. 5146–5154.*

Tokutake et al, Bioorganic & Medicinal Chemistry, vol. 6, No. 10 pp. 1935–1953 (1998).*

Katoh et al, Bioorganic & Medicinal Chemistry, vol. 6 no 13, pp. 1437–1442 (1996).*

Berger, U.V. & Schwab, M.E. N–Acetylated Alpha–Linked Acidic Dipeptides may be Involved in Axon–Schwann Cell Signaling. *J. Neurocytology* 25, 499–512 (1996).

Jackson, P.F. et al. Design, Synthesis, and Biological Activity of a Potent Inhibitor of the Neuropeptidase N–Acetylated Alpha–Linked Acidic Dipeptidase. *J. Med. Chem.* 39, 619–622 (1996).

Kozikowski, A.P. et al. Design of Remarkably Simple, Yet Potent Urea–Based Inhibitors of Glutamate Carboxypeptidase II (NAALADase). *J. Med. Chem.* 44, 298–301 (2001).

Lange, P.H. ProstaScint Scan for Staging Prostate Cancer. *Urology* 57, 402–406 (2001).

Nan, F. et al. Dual Function Glutamate–Related Ligands: Discovery of a Novel, Potent Inhibitor of Glutamate Carboxypeptidase II Possessing mGluR3 Agonist Activity. *J. Med. Chem.* 43, 772–774 (2000).

Neale, J.H. et al. N–Acetylaspartylglutamate: The Most Abundant Peptide Neurotransmitter in the Mammalian Central Nervous System. *J. Neurochem.* 75, 443–452 (2000).

Slusher, B.S. et al. Immunocytochemical Localization of the N–Acetyl–Aspartyl–Glutamate (NAAG) Hydrolyzing Enzyme N–Acetylated Alpha–Linked Acidic Dipeptidase (NAALADase). *J. Compar. Neuro.* 315, 217–229 (1992).

Stauch, B.L. et al. The effects of N–acetylated alpha–linked acidic dipeptidase (NAALADase) inhibitors on [$^3$H]NAAG catabolism in vivo. *Neurosci. Letters* 100, 295–300 (1989).

Subasinghe, N. et al. Synthesis of Acyclic and Dehydroaspartic Acid Analogues of Ac–Asp–Glu–OH and Their Inhibition of Rat Brain N–Acetylated Alpha–Linked Acidic Dipeptides (NAALADipeptidase). *J. Med. Chem.* 33, 2734–2744 (1990).

* cited by examiner

*Primary Examiner*—Paul J. Killos
*Assistant Examiner*—Hector M. Reyes
(74) *Attorney, Agent, or Firm*—Ropes & Gray LLP

(57) ABSTRACT

The instant invention provides reagents and methods for diagnosis, detection and treatment of cancers (for example, prostate cancers). In particular, the invention provides methods to generate various functionalized PSMA ligands, and their uses in diagnosis, detection, imaging, and treatment of prostate cancers, especially those overexpressing PSMA.

47 Claims, 11 Drawing Sheets

A.

Guilford 11254-36

IRDye78

Guilford 11254-36/IRDye78

B.

Guilford
11254-36
Normal Phase

Notes
Unlabeled Molecule of Interest Stained with Ninhydrin (red)
------- = Mobile Phase Front
◄- = Desired NIR Fluorophore-Coupled Product
<- = Unlabeled Molecule of Interest
O = Origin Structure of the beta-AG/IRDye78 conjugate (beta-AG/78)

Structure of beta-AG

Beta-aspartyl-glutamate
Mol. Wt.: 262.22

Guilford 11254-36

| Compound | Ki (Range) | |
|---|---|---|
| Quisqualic Acid (52809-07-1) | 155 nM - 2μM (Non-Competitive) |  |
| β-NAAG (Spaglumic Acid; 4910-46-7) | 201-700 nM (Competitive) |  |
| Guilford-4 | 700 nM |  |
| 2-(phosphonomethyl) pentanedioic acid (PMPA; Guilford 3 | 98-275 pM |  |
| Guilford-7 | 1.9 nM |  |

Asp-Glu

N-Acetyl-β-Asp-Glu (β-NAAG)

β-Asp-Glu

2-PMPA

MODIFIED PSMA LIGANDS AND USES RELATED THERETO

REFERENCE TO RELATED APPLICATIONS

This application claims priority to U.S. Provisional application No. 60/267,055, filed on Feb. 7, 2001, the specifications of which is hereby incorporated by reference in its entirety.

BACKGROUND OF THE INVENTION

Prostate cancer is the second leading cause of cancer-related deaths in US men. It is estimated that 184,500 new cases of prostate cancer will be diagnosed in the United States in 1998, and over 39,200 deaths will result from this cancer.

Prostate-specific membrane antigen (PSMA) is a 120 kDa protein expressed in prostate tissues and was originally identified by reactivity with a monoclonal antibody designated 7E11-C5 (Horoszewicz et al., 1987, Anticancer Res. 7:927–935; U.S. Pat. No. 5,162,504). PSMA is characterized as a type II transmembrane protein sharing sequence identity with the transferrin receptor (Israeli et al., 1994, Cancer Res. 54:1807–1811). PSMA is a glutamate carboxy-peptidase that cleaves terminal carboxy glutamates from both the neuronal dipeptide N-acetylaspartylglutamate (NAAG) and gamma-linked folate polyglutamate. That is, expression of PSMA cDNA confers the activity of N-acetylated α-linked acidic dipeptidase or "NAALADase" activity (Carter et al., 1996, PNAS 93:749–753).

More importantly, PSMA is expressed in increased amounts in prostate cancer, and elevated levels of PSMA are also detectable in the sera of these patients (Horoszewicz et al., 1987, supra; Rochon et al., 1994, Prostate 25:219–223; Murphy et al., 1995, Prostate 26:164–168; and Murphy et al., 1995, Anticancer Res. 15:1473–1479). As a prostate carcinoma marker, PSMA is believed to serve as a target for imaging and cytotoxic treatment modalities for prostate cancer. Prostate carcinogenesis, for example, is associated with an elevation in PSMA abundance and enzymatic activity of PSMA. PSMA antibodies, particularly indium-111 labeled and tritium labeled PSMA antibodies, have been described and examined clinically for the diagnosis and treatment of prostate cancer. PSMA is expressed in prostatic ductal epithelium and is present in seminal plasma, prostatic fluid and urine.

SUMMARY OF THE INVENTION

Figure 1:
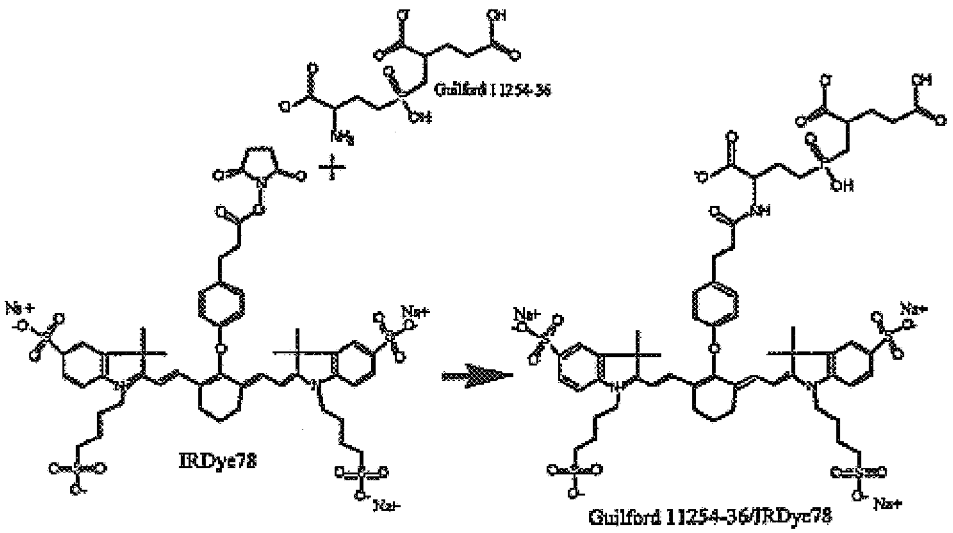
FIG. 1A. Guilford 11254-36 was conjugated under aqueous conditions to the near-infrared fluorophore IRDye78 (LI-COR, Lincoln, Nebr.; excitation 771 nm, emission 796 nm) using the chemistry shown.
FIG. 1B. The desired product of the reaction could be separated easily from reactants using normal phase thin-layer chromatography.
Figure 1:
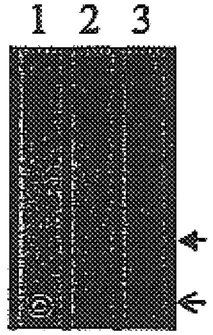

One aspect of the invention provides a compound represented in the general formula (Ia):

Ia

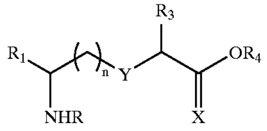

wherein:

X represents O or S;

Y represents:

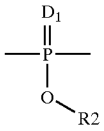, 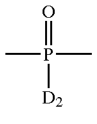, 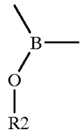, 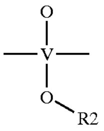 or 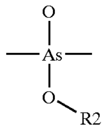

R represents a chelate ligand, a fluorescence tag, or a cytotoxic moiety;

R1 and R3, independently for each occurrence, represents an alkyl, an alkenyl, a cycloalkyl, a cycloalkenyl, an aryl, $—(CH_2)_m$-aryl, -alkyl-$CO_2R4$, -alkenyl-$CO_2R4$, -cycloalkyl-$CO_2R4$, -cycloalkenyl-$CO_2R4$ or -aryl-$CO_2R4$;

R2 and R4, independently for each occurrence, represent hydrogen, a lower alkyl, or a pharmaceutically acceptable salt;

$D_1$ represents O or S;

$D_2$ represents $N_3$, $SH_2$, $NH_2$, or $NO_2$;

m is 1, 2, 3 or 4; and, n is 0, 1, 2 or 3.

A related aspect provides a compound represented in the general formula (Ib):

Ib

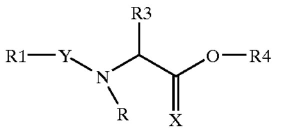

wherein X, Y, R, R1–R4, D1, D2, m and n are defined as above.

Another related aspect provides a compound represented in the general formula (Id):

Id

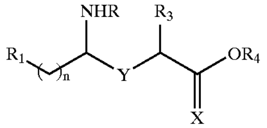

wherein X, Y, R, R1–R4, D1, D2, m and n are defined as above.

Another related aspect provides a compound represented in the general formula (Ie):

Ie

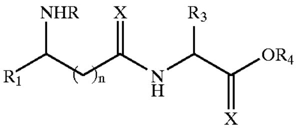

wherein X, Y, R, R1–R4, D1, D2, m and n are defined as above.

Another related aspect provides a compound represented in the general formula (If):

If

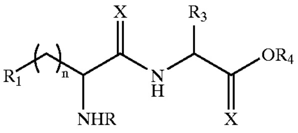

wherein X, Y, R, R1–R4, D1, D2, m and n are defined as above.

In a preferred embodiment, X represents O. In another preferred embodiment, R1 and R3 each independently represent a -lower alkyl-$CO_2R4$. In another preferred embodiment, Y represents —P(=O)(—OR2)—. In another preferred embodiment, R2 represents H or a lower alkyl. Most preferably, R2 represents H.

Another related aspect provides a compound represented in the general formula (Ic):

Ic

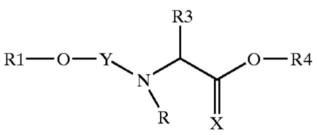

wherein X, Y, R, R1–R4, D1, D2, m and n are defined as above.

In a preferred embodiment, X represents O. In another preferred embodiment, R1 represent H, a -lower alkyl-$CO_2R4$, or $—(CH_2)_m$-aryl. In another preferred embodiment, Y represents —P(=O)(—OR2)—. In another preferred embodiment, R2 represents H or a lower alkyl. Most preferably, R represents H.

Another related aspect provides a compound represented in the general formula (II):

II

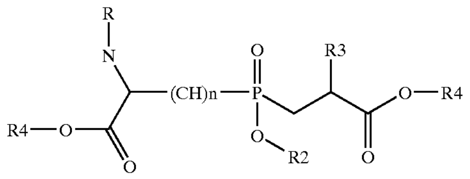

wherein:

R represents a chelate ligand, a fluorescence tag, or a cytotoxic moiety;

R3 represents an alkyl, an alkenyl, a cycloalkyl, a cycloalkenyl, an aryl, —$(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

m is 1, 2, 3 or 4; and, n is 0, 1, 2 or 3.

Another related aspect provides a compound represented in the general formula (III):

III

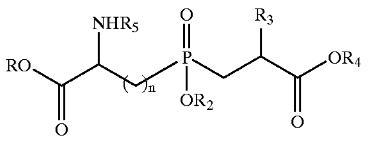

wherein:

R represents a chelate ligand, a fluorescence tag, or a cytotoxic moiety;

R3 represents an alkyl, an alkenyl, a cycloalkyl, a cycloalkenyl, an aryl, —$(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

R5 represents H or a lower alkyl;

m is 1, 2, 3 or 4; and n is 0, 1, 2 or 3.

Another related aspect provides a compound represented in the general formula (IV):

IV

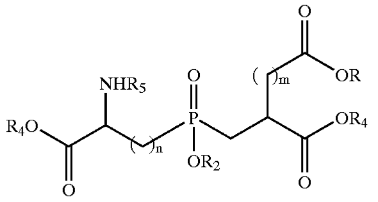

wherein R, R2–R5, m and n are defined above.

Another related aspect provides a compound represented in the general formula (V):

V

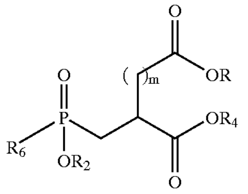

wherein

R represents a chelate ligand, a fluorescence tag, or a cytotoxic moiety;

R2 and R4, independently for each occurrence, represent hydrogen, a lower alkyl, or a pharmaceutically acceptable salt;

R6 represents an alkyl, an alkenyl, a cycloalkyl, a cycloalkenyl, an aryl, or —$(CH_2)_m$-aryl; and, m is 1, 2, 3 or 4.

In a preferred embodiment, R is at least 25 amu in size, more preferably, at least 50 amu, at least 100 amu in size, or at least 250 amu in size.

In another preferred embodiment, R is a cytotoxic moiety, and R is hydrolyzable from the PSMA ligand.

In another preferred embodiment, R is linked to the rest of the molecule by use of an amide or ester group. For example, R can be linked to the rest of the molecule by use of an acid labile or base-cleavable linker.

In another preferred embodiment, R is a chelate moiety for chelating a metal. For example, R can be a chelator for a radiometal or a paramagnetic ion. Specifically, R can be a chelator for a radionuclide useful for radiotherapy or imaging procedures. In a preferred embodiment, R is chelator for a beta- or alpha-emitter for radio-therapeutic use. In another preferred embodiment, R can be chelator for a gamma-emitter, positron-emitter, Auger electron-emitter, X-ray emitter or flourescence-emitter. In a most preferred embodiment, R is $^{99m}$Tc (technium).

In another preferred embodiment, R is a radiosensitizing agent selected from: nitroimidazoles, metronidazole or misonidazole.

In another preferred embodiment, R is a bifunctional chelator $N_xS_y$ that are capable of coordinately binding a metal or radiometal, wherein x and y are integers between 1 and 4. $N_xS_y$ can have a $N_2S_2$ or a $N_3S$ core.

In another preferred embodiment, R is Boron addend.

In another preferred embodiment, R is a chemotherapeutic agent.

In another preferred embodiment, R is a drug that interferes with intracellular protein synthesis.

In another preferred embodiment, R is a prodrug that is only activated from its inactive precursor form by host metabolism.

In another preferred embodiment, R is a toxin selected from: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin or volkensin.

In another preferred embodiment, R is an enzyme that converts prodrug locally.

Another aspect of the invention provides a pharmaceutical composition comprising the compound of any one of the modified PSMA ligands of the instant invention, and a pharmaceutically acceptable carrier.

Another aspect of the invention provides a method for detecting or imaging PSMA (prostate-specific membrane antigen)-expressing cells in a patient, comprising:

(a) contacting the patient with a modified PSMA ligand of any one of claims 1–5, 11, and 17–20;

(b) detecting the modified PSMA ligand, thereby detecting PSMA-expressing cells in the patient.

In a preferred embodiment, the PSMA-expressing cells are prostatic cells in prostatic hyperplasia or prostate cancer. In another preferred embodiment, the modified PSMA ligand is modified by an imaging agent. For example, the imaging agent is a radionuclide imaging agent. The radionuclide imaging agent can be radioactive iodine or indium.

In another preferred embodiment, the modified PSMA ligand is detected by radioscintigraphy, magnetic resonance imaging (MRI), computed tomography (CT scan), or positron emission tomography (PET).

In another preferred embodiment, the contacting step (a) is effected by administering to the patient the modified PSMA ligand. In another preferred embodiment, the detecting step (b) includes determining the volume, shape and/or location of PSMA-expressing cells in the patient.

Another aspect of the invention provides a method for determining the abundance of PSMA in a sample, comprising:

(a) contacting the sample with any one of the modified PSMA ligands of claims 1–5, 11, and 17–20;

(b) determining the abundance of the modified PSMA ligands bound to PSMA, or the abundance of the modifying group of said bound ligands, thereby determining the abundance of PSMA in said sample.

In a preferred embodiment, the sample is prostatic fluid, urine, or obtained from seminal plasma.

Another aspect of the invention provides a method to diagnose, in a test sample, the presence of a prostate disease condition associated with PSMA-overexpression, comprising:

(a) using the method of determining the abundance of PSMA in the test sample and a normal control sample;

(b) comparing the level of abundance of PSMA in the test sample and the control sample;

wherein statistically significant higher levels of abundance of PSMA in the test sample indicates the presence of a prostate disease condition associated with PSMA-overexpression.

Another aspect of the invention provides a method to treat a patient suffering from a disease condition associated with PSMA-overexpression, comprising administering to the patient an effective amount of modified PSMA ligand of the instant invention.

In a preferred embodiment, the disease condition is prostatic hyperplasia or prostate cancer. In another preferred embodiment, the modified PSMA ligand is modified by a cytotoxic agent In another preferred embodiment, the modified PSMA ligand is modified by a radiometal chelating agent. In a preferred embodiment, the method further comprises infusing into the patient an effective amount of chelator compounds, which can be EDTA or DTPA. In a preferred embodiment, the modified PSMA ligand is administered to the patient at a dose that contain 10–100 times less active agent as an active moiety than the dosage of agent administered as unconjugated active agents.

Another aspect of the invention provides a kit for diagnosing or detecting the presence of a PSMA, comprising: a) at least one of the modified PSMA ligand of any one of claims 1–5, 11, and 17–20; b) an instruction.

In a preferred embodiment, the modified PSMA ligand contains a chelate moiety for chelating a metal or a paramagnetic ion. In another preferred embodiment, the kit further comprises at least one metal. For example, the metal can be a radionuclide useful for radiotherapy or imagine procedures.

Another aspect of the invention provides a method to treat a patient suffering from a disease condition associated with PSMA-overexpression, comprising administering to the patient an effective amount of IRDye78.

DETAILED DESCRIPTION OF THE INVENTION

(i) Overview

The present invention is directed to improved reagents for detecting cells based on NAALADase activity, PSMA binding, and/or for selective killing of cells in a NAALADase-dependent manner. The invention derives in part from the discovery that relatively large functionalities can be added to modified PSMA ligands without disrupting the binding of those inhibitors to the enzyme. Accordingly, modified PSMA ligands can be derivitized with, and used to selectively deliver, such secondary functionalities as cytotoxic agents, radiometal chelating agents, fluoremetric agents and other imaging agents. For ease of reading, these compounds are referred to herein as the subject "modified (or functionalized) PSMA ligands."

One aspect of the present invention provides a method for detecting or identifying cells which express a NAALADase activity, e.g., PSMA, and can be used for example to detect the presence of prostatic hyperplasia or prostate cancer. According to the present invention, the modified PSMA ligand may be an imaging agent. Imaging agents are useful diagnostic procedures as well as the procedures used to identify the location of metastasized cells. For instance, imaging using the subject modified PSMA ligands, e.g., those including an imaging agent functionality, can be performed by radioscintigraphy, magnetic resonance imaging (MRI or computed tomography (CT scan). The most commonly employed radionuclide imaging agents include radioactive iodine and indium. Imaging by CT scan may employ a heavy metal such as iron chelates. MRI scanning may employ chelates of gadolinium or manganese. Additionally, positron emission tomography (PET) may be possible using positron emitters of oxygen, nitrogen, iron, carbon, or gallium. For instance, the subject modified PSMA ligands, e.g., those including a imaging agent functionality, can be administered to a patient and used as part of a detection protocol to image tissue in a manner dependent on the level of expression of PSMA. In such a manner, the volume, shape and location of hyperproliferative prostate tissue can be imagined in the body.

In a related assay, forms of the modified PSMA ligand which are amenable to detection by, e.g., spectrometric techniques or scintillation, can be used to determine the level of PSMA in samples of prostate tissue or bodily fluid, and compared to reference samples, in to ascertain the PSMA levels/NAALADase activity relative to normal prostate tissue.

Another aspect of the invention utilizes forms of the modified PSMA ligands to selectively ablate tissue having elevated levels of PSMA, e.g., as part of a therapeutic regimen to lessen the severity of prostatic hyperplasia or prostate cancer. In such embodiments, versions of the modified PSMA ligand which include such secondary functionalities as cytotoxic agents or radiometal chelating agents can be used.

Still another aspect of the invention provides compositions and kits including the subject modified PSMA ligands.

(ii) Definitions

Before describing exemplary embodiments, there is provided certain definitions for terms used in the specification and claims.

"NAAG" refers to N-acetyl-aspartyl-glutamate, an important peptide component of the brain, with levels comparable to the major inhibitor neurotransmitter gamma-aminobutyric acid (GABA). NAAG is neuron-specific, present in synaptic vesicles and released upon neuronal stimulation in several systems presumed to be glutamatergic. Studies suggest that NAAG may function as a neurotransmitter and/or neuromodulator in the central nervous system, or as a precursor of the neurotransmitter glutamate. "Beta-NAAG" or "β-NAAG" is a molecule similar to the natural substrate NAAG. β-NAAG replaces the natural Asp-Glu linkage with a linkage of Glu to the beta-carbon of Asp. β-NAAG is a non-hydrolizable competitive inhibitor of PSMA. "Beta-AG" or "β-AG" is essentially the same as beta-NAAG except that it lacks the N-acetyl moiety (see FIG. 6, lower panel). Beta-NAAG can not be hydrolyzed by PSMA.

"NAALADase" refers to N-acetylated α-linked acidic dipeptidase, a membrane-bound metallopeptidase which catabolizes NAAG to N-acetylaspartate (NAA) and glutamate (GLU):

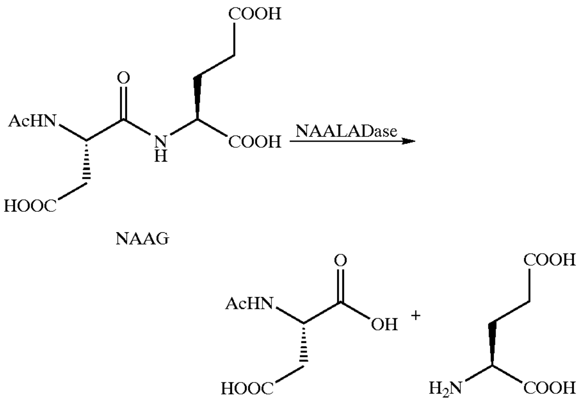

NAAG

NAA + GLU

NAALADase shows a high affinity for NAAG with a $K_m$ of 540 nM. If NAAG is a bioactive peptide, then NAALADase may serve to inactivate NAAG's synaptic action. Alternatively, if NAAG functions as a precursor for glutamate, the primary function of NAALADase may be to regulate synaptic glutamate availability.

The term "prevention," in relation to tumor growth or tumor cell growth, means no tumor or tumor cell growth if none had occurred, no further tumor or tumor cell growth if there had already been growth.

The term "prostate disease" relates to prostate cancer such as adenocarcinoma or metastatic cancers, conditions characterized by abnormal growth of prostatic epithelial cells such as benign prostatic hyperplasia, and other conditions requiring treatment by the compounds of the present invention.

"PSA" refers to Prostate Specific Antigen, a well known prostate cancer marker. It is a protein produced by prostate cells and is frequently present at elevated levels in the blood of men with prostate cancer. PSA correlates with tumor burden, serves as an indicator of metastatic involvement, and provides a parameter for following a prostate cancer patient's response to surgery, irradiation and androgen replacement therapy.

"PSMA" refers to Prostate Specific Membrane Antigen, a potential prostate carcinoma marker that has been hypothesized to serve as a target for imaging and cytotoxic treatment modalities for prostate cancer. PSMA is expressed in prostatic ductal epithelium and is present in seminal plasma, prostatic fluid and urine. It has been found that the expression of PSMA cDNA confers the activity of NAALADase.

The term "treatment" refers to any process, action, application, therapy, or the like, wherein an animal, including a human being, is subject to medical aid with the object of improving the animal's condition, directly or indirectly.

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The terms "alkenyl" and "alkynyl" refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, $—O—(CH_2)_m—R_8$, where m is zero or an integer in the range of 1 to 6, and $R_8$ represents a substituted or unsubstituted aryl, an aralkyl, a cycloalkyl, a cycloalkenyl, or a heterocycle.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$–$C_{30}$ for straight chains, $C_3$–$C_{30}$ for branched chains), and more preferably 20 or fewer. Likewise, preferred cycloalkyls have from 3–10 carbon atoms in their ring structure, and more preferably have 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethylthio, and the like.

The terms "amine" and "amino" are art-recognized and refer to both unsubstituted and substituted amines, e.g., a moiety that can be represented by the general formula:

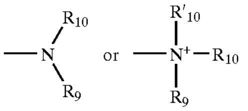

wherein $R_9$, $R_{10}$ and $R'_{10}$ each independently represent a hydrogen, an alkyl, an alkenyl, —$(CH_2)_m$—$R_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, a heterocycle or a polycycle; and m is zero or an integer in the range of 1 to 8. In preferred embodiments, only one of $R_9$ or $R_{10}$ can be a carbonyl, e.g., $R_9$, $R_{10}$ and the nitrogen together do not form an imide. In even more preferred embodiments, $R_9$ and $R_{10}$ (and optionally $R'_{10}$) each independently represent a hydrogen, an alkyl, an alkenyl, or —$(CH_2)_m$—$R_8$. Thus, the term "alkylamine" as used herein means an amine group, as defined above, having a substituted or unsubstituted alkyl attached thereto, i.e., at least one of $R_9$ and $R_{10}$ is an alkyl group.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from heteroatoms (preferably 1 to 4), for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle", as used herein, refers to an aromatic or non-aromatic ring in which each atom of the ring is carbon.

The term "carbonyl" is art-recognized and includes such moieties as can be represented by the general formula:

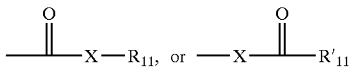

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$ where m and $R_8$ are as defined above. Where X is an oxygen and $R_{11}$ or $R'_{11}$ is not hydrogen, the formula represents an "ester." Where X is an oxygen, and $R_{11}$ is as defined above, the moiety is referred to herein as a carboxyl group, and particularly when $R_{11}$ is a hydrogen, the formula represents a "carboxylic acid." Where X is an oxygen, and $R'_{11}$, is hydrogen, the formula represents a "formate." In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "heteroatom" as used herein means an atom of any clement other than carbon or hydrogen. Preferred heteroatoms are boron, nitrogen, oxygen, phosphorus, sulfur and selenium.

The terms "heterocyclyl" or "heterocyclic group" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2^-$.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings." Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, 2nd ed.; Wiley: New York, 1991).

The term "modifying group" or "functional group" refers to the functional "R groups" of the modified PSMA ligands. It could be a fluorescent tag, a chelate ligand, a cytotoxic moiety, or any other functional groups.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g., alkyl, m, n, etc., when it occurs more than once in any structure, is intended to be independent of its definition elsewhere in the same structure.

Certain compounds of the present invention may exist in particular geometric or stercoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., the ability to bind to PSMA), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

(iii) Exemplary Modified PSMA Ligands

The natural substrate for PSMA is the dipeptide N-Acetyl-L-Asp-L-Glu (NAAG). The first competitive inhibitor described for PSMA (Serval etal., J. Neurochemistry, 1990, 55: 39–46) is beta-NAAG, a molecule similar to the natural substrate NAAG. Beta-NAAG replaces the natural Asp-Glu linkage with a linkage of Glu to the beta-carbon of Asp (see modeling below). Since the N-acetyl moiety of NAAG is reportedly not essential for NAALADase specificity (Serval etal., J. Neurochemistry, 1990, 55: 39–46), it is our prediction that the N-terminus of NAAG or beta-NAAG may not participate directly in binding the enzyme, and thus modifications of the N-terminus of NAAG, beta-NAAG, beta-AG, or other PSMA ligands by extension with functional groups (e.g. fluorophore, radiometal chelators, cytotoxic agents, etc.) may not dramatically affect the binding affivnity to PSMA.

Figure 9:
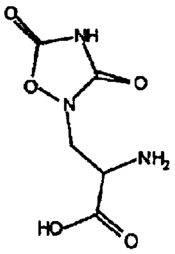
FIG. 9. Structural comparison of a few known inhibitors of PSMA.
Figure 9:
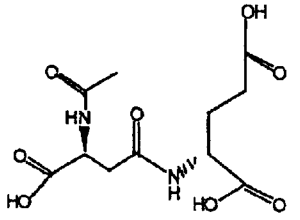
Figure 9:
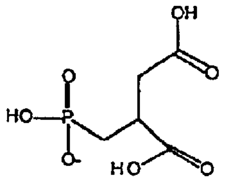
Figure 9:
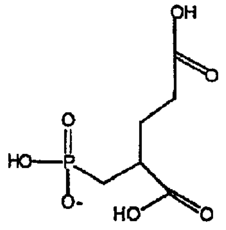
Figure 9:
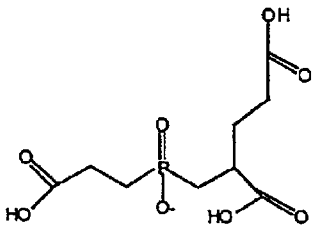

In fact, a direct comparison of the chemical structures of several potential PSMA ligands, namely NAAG, beta-NAAG, a non-competitive inhibitor called quisqualic acid, and a high affinity compound synthesized by Zeneca and Guilford pharmaceuticals called 2-PMPA (molecule 3 in Jackson et al., J. Med. Chem. 1996, 39: 619–622), yields valuable information regarding the structural characteristics of PSMA binding region (FIG. 9).

While all depicted compounds and their derivatives are PSMA ligands with various degrees of inhibitory functions, it is contemplated that in a preferred embodiment of the invention, there is a precise spacing of carboxylic acid residues on the right hand side of PSMA ligands, and a localization of negative charge at the left hand side of each molecule. In another preferred embodiment of the invention, the region to the left of the PSMA binding site (for example, the left of the phosphate group of the Guilford compound 3) can be further extended to accommodate addition of modification groups, without significant loss of affinity/inhibitory activity for PSMA (FIG. 9).

There are many conceivable ways to modify these PSMA ligands. For example, in a preferred embodiment, an extended region can be added to the left of the Guilford compound 3, which further includes at least one —NH2 group for conjugation of modification groups (see below).

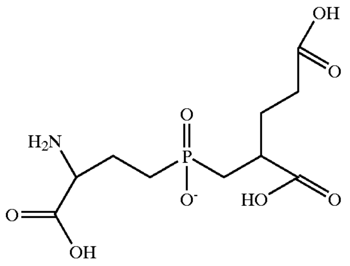

Careful analysis reveals that this compound is actually an amino acid with an unnatural R-group, and chemical synthesis may be simplified using this perspective. Also, such a molecule is chiral with respect to the "alpha" carbon, and hence two possible enantiomers can both be tested.

Alternatively, in another preferred embodiment, the amino (or other coupling group) could be coupled to the first methylene group (see below):

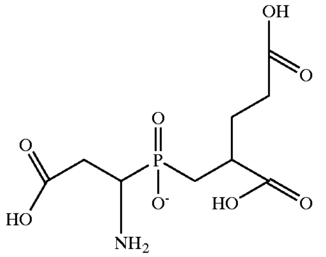

In another preferred embodiment, a modification group can be added to the —NH2 group in β-AG or its derivative, while in another preferred embodiment, a modification group can be added to the —NH— group in AG or its derivative.

Figure 10:
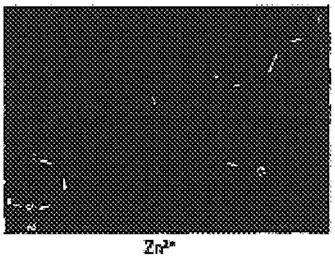
FIG. 10. Computer-aided 3-D molecular modeling of PSMA ligands. The 3-D molecular modeling was performed using MM2 energy minimization (CS Chem3D Pro software) in the presence of the $Zn^{2+}$ atom known to be at the catalytic site of PSMA. By comparing the structures of PSMA natural substrate L-Asp-L-Glu to various inhibitors, it was revealed that the spacing of carboxylic acids and negative charge plays important role in determining binding affinity. The presence of the N-acetyl group or a complete Asp molecule is not required for binding.
Figure 10:
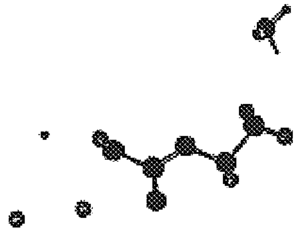
Figure 10:
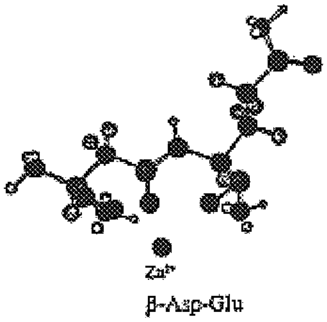
Figure 10:
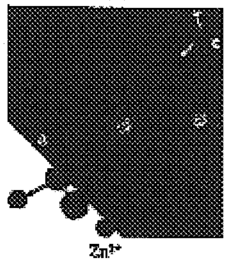
Figure 10:
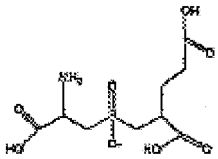

Maintenance of binding affinity by these modifications can be routinely determined empirically. Computer modeling may also be used to aid the design of certain modifications, as exemplified in FIG. 10. For both of these preferred compounds, functional groups can be added to the free amino group by a single step coupling using NHS-esters or EDC activated carboxyl groups, thus generating functionalized or modified PSMA ligands useful for cancer detection and/or treatment. Additional spacing atoms between the amino group of the above two compounds and the functional group can be routinely determined empirically.

Figure 11:
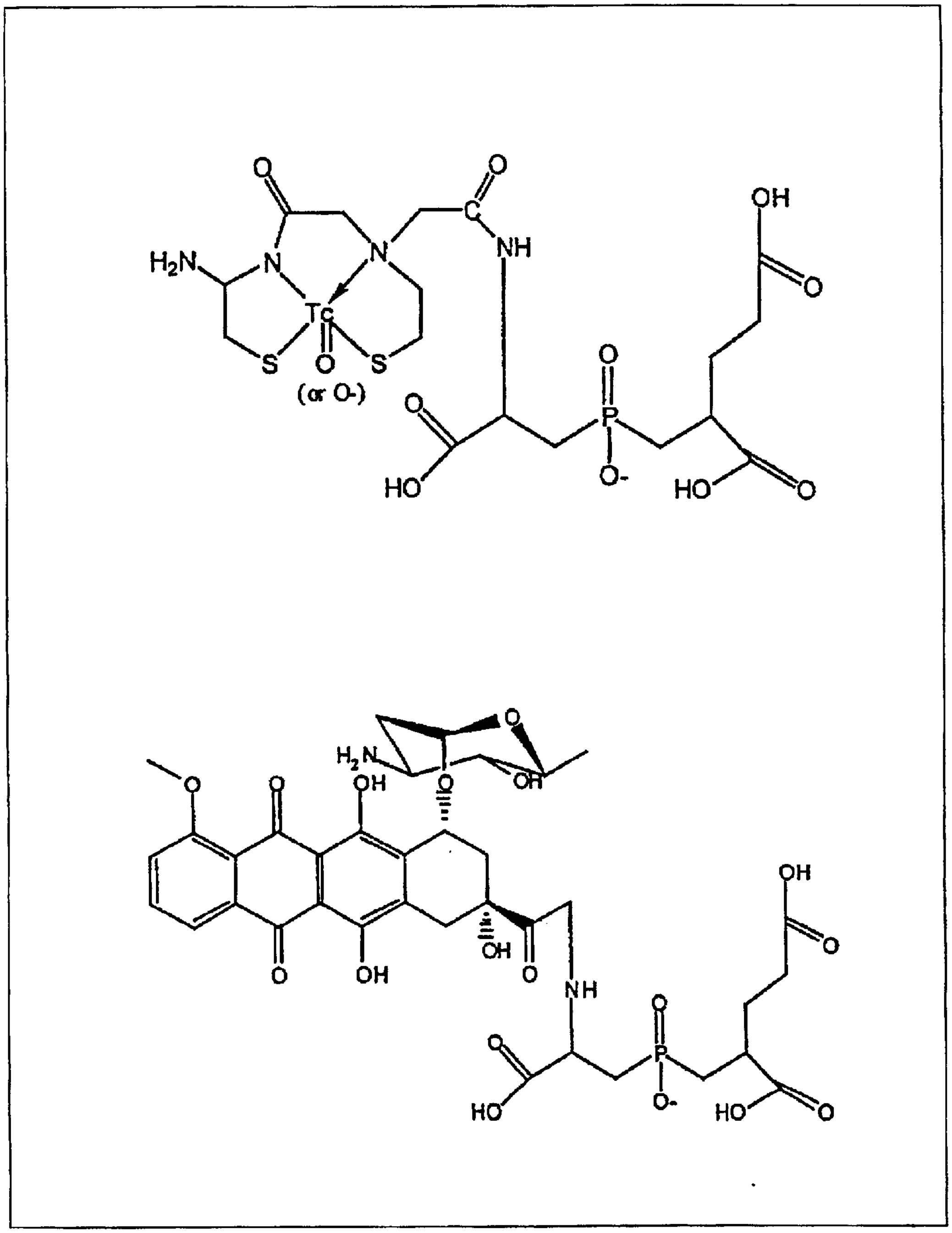
FIG. 11. Two exemplary modified PSMA ligands. Top panel shows a radioscintigraphic probe for prostate cancer detection comprising a radiometal chelator coupled to the primary amine of Guilford 11254-36. Bottom panel shows a cytotoxic drug for prostate cancer treatment comprising doxorubicin coupled to Guilford 11254-36.

For example, FIG. 11 shows two exemplary modified PSMA ligands that utilizes the primary amine of one of the listed preferred compounds to conjugate functional groups.

In one embodiment, the subject modified PSMA ligand is represented in the general formula (Ia):

Ia

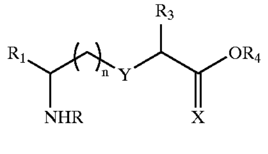

Wherein:

X represents O or S;

Y represents:

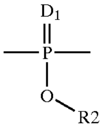 , 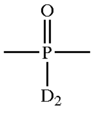 , 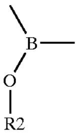 , 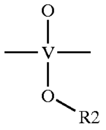 or 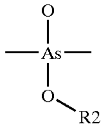

R represents a chelate ligand, a fluorescence tag, or a cytotoxic moiety;

R1 and R3, independently for each occurrence, represents an alkyl, an alkenyl, a cycloalkyl, a cycloalkenyl, an aryl, $-(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

$D_1$ represents O or S;

$D_2$ represents $N_3$, $SH_2$, $NH_2$, or $NO_2$;

m is 1, 2, 3 or 4; and, n is 0, 1, 2 or 3.

In other embodiments, the subject modified PSMA ligand is represented in the general formula (Ib):

Ib

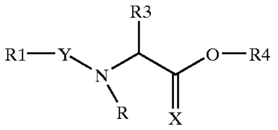

wherein X, Y, R, R1, R3 and R4 are as defined above.

In other embodiments, the subject modified PSMA ligand is represented in the general Ic

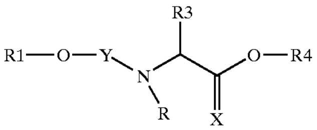

wherein X, Y, R, R1, R3 and R4 are as defined above.

In other embodiments, the subject modified PSMA ligand is represented in the general formula (Id):

Id

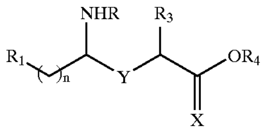

wherein X, Y, R, R1, R3 and R4 are as defined above.

In other embodiments, the subject modified PSMA ligand is represented in the general formula (Ie):

Ie

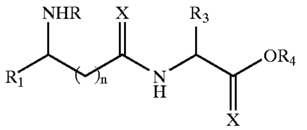

wherein X, Y, R, R1, R3 and R4 are as defined above.

In other embodiments, the subject modified PSMA ligand is represented in the general formula (If):

If

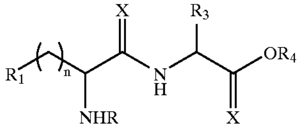

wherein X, Y, R, R1, R3 and R4 are as defined above.

In certain preferred embodiments of compounds Ia, Ib, Id–If. X represents O; R1 and R3 each independently represent a -lower alkyl-$CO_2$R4; Y represents —P(═O)(—OR2)—; and R2 represents H or a lower alkyl, and more preferably H.

In certain preferred embodiments of compound Ic: X represents O; R1 represent H or a -lower alkyl-$CO_2$R4; —$(CH_2)_m$-aryl; Y represents —P(═O)(—OR2)—; and R2 represents H or a lower alkyl, and more preferably H.

Unless apparent from the context, references to "formula I" throughout the application mean any one of formulas Ia–If.

For example, the subject modified PSMA ligand may be represented in the general formula (II):

II

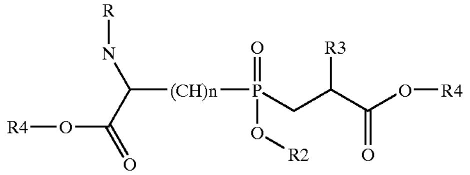

R represents a chelate ligand, a fluorescence tag, or a cytotoxic moiety;

R3 represents an alkyl, an alkenyl, a cycloalkyl, a cycloalkenyl, an aryl, —$(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

m is 1, 2, 3 or 4; and, n is 0, 1, 2 or 3.

In yet other embodiments, the chelate ligand, fluorescence tag or a cytotoxic moiety can be covalently linked via one of the carboxylic groups, e.g., as represented in Formula III, or IV:

III

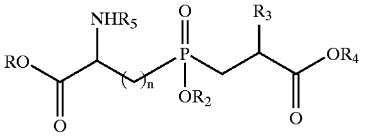

IV

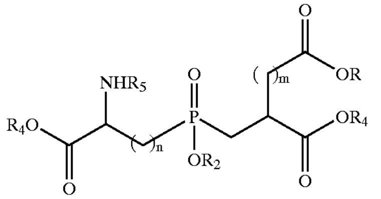

Wherein:

R represents a chelate ligand, a fluorescence tag, or a cytotoxic moiety;

R3 represents an alkyl, an alkenyl, a cycloalkyl, a cycloalkenyl, an aryl, —$(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

R5 represents H or a lower alkyl;

m is 1, 2, 3 or 4; and n is 0, 1, 2 or 3.

In still other embodiments, the subject modified PSMA ligand is represented in Formula V:

V

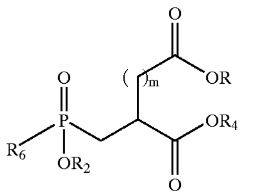

wherein

R represents a chelate ligand, a fluorescence tag, or a cytotoxic moiety;

R2 and R4, independently for each occurrence, represent hydrogen, a lower alkyl, or a pharmaceutically acceptable salt;

R6 represents an alkyl, an alkenyl, a cycloalkyl, a cycloalkenyl, an aryl, or —$(CH_2)_m$-aryl; and, m is 1, 2, 3 or 4.

In many embodiments of the subject ligands, the secondary functionality R will be relatively large, e.g., at least 25 amu in size, and in many instances can be at least 50, 100 or 250 amu in size.

In certain preferred embodiments, particularly where R is a cytotoxic moiety, R is hydrolyzable from the PSMA ligand, e.g., such as may be provided by use of an amide or ester group linking R to the rest of the molecule.

In certain preferred embodiments, R is a chelate moiety for chelating a metal, e.g., a chelator for a radiometal or paramagnetic ion. In preferred embodiments, R is a chelator for a radionuclide useful for radiotherapy or imaging procedures. Radionuclides useful within the present invention include gamma-emitters, positron-emitters, Auger electron-emitters, X-ray emitters and fluorescence-emitters, with beta- or alpha-emitters preferred for therapeutic use. Examples of radionuclides useful as toxins in radiation therapy include: $^{32}P$, $^{33}P$, $^{43}K$, $^{47}Sc$, $^{52}Fe$, $^{57}Co$, $^{64}Cu$, $^{67}Ga$, $^{67}Cu$, $^{68}Ga$, $^{71}Ge$, $^{75}Br$, $^{76}Br$, $^{77}Br$, $^{77}As$, $^{77}Br$, $^{81}Rb/^{81M}Kr$, $^{87M}Sr$, $^{90}Y$, $^{97}Ru$, $^{99}Tc$, $^{100}Pd$, $^{101}Rh$, $^{103}Pb$, $^{105}Rh$, $^{109}Pd$, $^{111}Ag$, $^{111}In$, $^{113}In$, $^{119}Sb$ $^{121}Sn$, $^{123}I$, $^{125}I$, $^{127}Cs$, $^{128}Ba$, $^{129}Cs$, $^{131}I$, $^{131}Cs$, $^{143}Pr$, $^{153}Sm$, $^{161}Tb$, $^{166}Ho$, $^{169}Eu$, $^{177}Lu$, $^{186}Re$, $^{188}Re$, $^{189}Re$, $^{191}Os$, $^{193}Pt$, $^{194}Ir$, $^{197}Hg$, $^{199}Au$, $^{203}Pb$, $^{211}At$, $^{212}Pb$, $^{212}Bi$ and $^{213}Bi$. Preferred therapeutic radionuclides include $^{188}Re$, $^{186}Re$, $^{203}Pb$, $^{212}Pb$, $^{212}Bi$, $^{109}Pd$, $^{64}Cu$, $^{67}Cu$, $^{90}y$, $^{125}I$, $^{131}I$, $^{77}Br$, $^{211}At$, $^{97}Ru$, $^{105}Rh$, $^{198}Au$ and $^{199}Ag$, $^{166}Ho$, or $^{177}Lu$. Conditions under which a chelator will coordinate a metal are described, for example, by Gansow et al., U.S. Pat. Nos. 4,831,175, 4,454,106 and 4,472,509.

$^{99m}Tc$ is a particularly attractive radioisotope for therapeutic and diagnostic applications, as it is readily available to all nuclear medicine departments, is inexpensive, gives minimal patient radiation doses, and has ideal nuclear imaging properties. It has a half-life of six hours which means that rapid targeting of a technetium-labeled antibody is desirable. Accordingly, in certain preferred embodiments, the modified PSMA ligand includes a chelating agents for technium.

R can also be a radiosensitizing agents, e.g., a moiety that increase the sensitivity of cells to radiation. Examples of radiosensitizing agents include nitroimidazoles, metronidazole and misonidazole (see: DeVita, V. T. Jr. in Harrison's Principles of Internal Medicine, p.68, McGraw-Hill Hill Book Co., New York 1983, which is incorporated herein by reference). The modified PSMA ligand that comprises a radiosensitizing agent as the active moiety is administered and localizes at the metastasized cell. Upon exposure of the individual to radiation, the radiosensitizing agent is "excited" and causes the death of the cell.

There are a wide range of moieties which can serve as chelating ligands and which can be derivatized to the PSMA inhibitors. For instance, the chelating ligand can be a derivative of 1,4,7,10-tetraazacyclododecanetetraacetic acid (DOTA), ethylenediaminetetraacetic acid (EDTA), diethylenetriaminepentaacetic acid (DTPA) and 1-p-Isothiocyanato-benzyl-methyl-diethylenetriaminepentaacetic acid (ITC-MX). These chelators typically have groups on the side chain by which the chelator can be used for attachment to a PSMA inhibitor. Such groups include, e.g., benzylisothiocyanate, by which the DOTA, DTPA or EDTA can be coupled to, e.g., an amine group of the inhibitor.

In one embodiment, R is an "$N_xS_y$" chelate moiety. As defined herein, the term "$N_xS_y$ chelates" includes bifunctional chelators that are capable of coordinately binding a metal or radiometal and, preferably, have $N_2S_2$ or $N_3S$ cores. Exemplary $N_xS_y$ chelates are described, e.g., in Fritzberg et al. (1988) PNAS 85:4024–29; and Weber et al. (1990) Bioconjugate Chem. 1:431-37; and in the references cited therein The Jacobsen et al. PCT application WO 98/12156 provides methods and compositions, i.e. synthetic libraries of binding moieties, for identifying compounds which bind to a metal atom. The approach described in that publication can be used to identify binding moieties which can subsequently be added to PSMA ligands to derive the modified PSMA ligands of the present invention.

A problem frequently encountered with the use of conjugated proteins in radiotherapeutic and radiodiagnostic applications is a potentially dangerous accumulation of the radiolabeled moiety fragments in the kidney. When the conjugate is formed using a acid-or base-labile linker, cleavage of the radioactive chelate from the protein can advantageously occur. If the chelate is of relatively low molecular weight, as most of the subject modified PSMA ligands are expected to be, it is not retained in the kidney and is excreted in the urine, thereby reducing the exposure of the kidney to radioactivity. However, in certain instances, it may be advantageous to utilize acid-or base-labile linkers in the subject ligands for the same reasons they have been used in labeled proteins.

Accordingly, certain of the subject modified PSMA ligands can be synthesized, by standard methods known in the art, to provide reactive functional groups which can form acid-labile linkages with, e.g., a carbonyl group of the ligand. Examples of suitable acid-labile linkages include hydrazone and thiosemicarbazone functions. These are formed by reacting the oxidized carbohydrate with chelates bearing hydrazide, thiosemicarbazide, and thiocarbazide functions, respectively.

Alternatively, base-cleavable linkers, which have been used for the enhanced clearance of the radiolabel from the kidneys, can be used. See, for example, Weber et al. 1990 Bioconjug. Chem. 1:431. The coupling of a bifunctional chelate to a PSMA ligand via a hydrazide linkage can incorporate base-sensitive ester moieties in a linker spacer arm. Such an ester-containing linker unit is exemplified by ethylene glycolbis(succinimidyl succinate), (EGS, available from Pierce Chemical Co., Rockford, Ill.), which has two terminal N-hydroxysucciuimide (NHS) ester derivatives of two 1,4-dibutyric acid units, each of which are linked to a single ethylene glycol moiety by two alkyl esters. One NHS ester may be replaced with a suitable amine-containing BFC (for example 2-aminobenzyl DTPA), while the other NHS ester is reacted with a limiting amount of hydrazine. The resulting hyrazide is used for coupling to the PSMA ligand, forming an ligand-BFC linkage containing two alkyl ester functions. Such a conjugate is stable at physiological pH, but readily cleaved at basic pH.

PSMA ligands labeled by chelation are subject to radiation-induced scission of the chelator and to loss of radioisotope by dissociation of the coordination complex. In some instances, metal dissociated from the complex can be re-complexed, providing more rapid clearance of non-specifically localized isotope and therefore less toxicity to non-target tissues. For example, chelator compounds such as EDTA or DTPA can be infused into patients to provide a pool of chelator to bind released radiometal and facilitate excretion of free radioisotope in the urine.

In still other embodiments, R is a Boron addend, such as a carborane. For example, carboranes can be prepared with carboxyl functions on pendant side chains, as is well known in the art. Attachment of such carboranes to an amine functionality, e.g., as may be provided on the PSMA ligand, can be achieved by activation of the carboxyl groups of the carboranes and condensation with the amine group to produce the conjugate. Such modified PSMA ligands can be used for neutron capture therapy.

In still other embodiments, the modified PSMA ligand includes a cytotoxic moiety as the R functionality, such as a chemotherapeutic agent or a toxin. Many drugs and toxins are known which have cytotoxic effects on cells, and can be used in connection with the present invention. They are to be found in compendia of drugs and toxins, such as the Merck Index, Goodman and Gilman, and the like, and in the references cited above.

Chemotherapeutics useful as active moieties which when conjugated to a modified PSMA ligand are specifically delivered to metastasized colorectal cells are typically, small chemical entities produced by chemical synthesis. Chemotherapeutics include cytotoxic and cytostatic drugs. Chemotherapeutics may include those which have other effects on cells such as reversal of the transformed state to a differentiated state or those which inhibit cell replication Examples of known cytotoxic agents useful in the present invention are listed, for example, in Goodman et al., "The Pharmacological Basis of Therapeutics," Sixth Edition, A. G. Gilman et al, eds./Macmillan Publishing Co. New York, 1980. These include taxol, nitrogen mustards, such as mechlorethamine, cyclophosphamide, melphalan, uracil mustard and chlorambucil; ethylenimine derivatives, such as thiotepa; alkyl sulfonates, such as busulfan; nitrosoureas, such as carmustine, lomustine, semustine and streptozocin; triazenes, such as dacarbazine; folic acid analogs, such as methotrexate; pyrimidine analogs, such as fluorouracil, cytarabine and azaribine; purine analogs, such as mercaptopurine and thioguanine; vinca alkaloids, such as vinblastine and vincristine; antibiotics, such as dactinomycin, daunorubicin, doxorubicin, bleomycin, mithramycin and mitomycin; enzymes, such as L-asparaginase; platinum coordination complexes, such as cisplatin; substituted urea, such as hydroxyurea; methyl hydrazine derivatives, such as procarbazine; adrenocortical suppressants, such as mitotane; hormones and antagonists, such as adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), and androgens (testosterone propionate and fluoxymesterone).

Drugs that interfere with intracellular protein synthesis can also be used; such drugs are known to these skilled in the art and include puromycin, cycloheximide, and ribonuclease.

Prodrugs forms of the chemotherapeutic moiety are especially useful in the present invention to generate an inactive precursor.

Most of the chemotherapeutic agents currently in use in treating cancer possess functional groups that are amenable to chemical crosslinking directly with an amine or carboxyl group of a PSMA ligand. For example, free amino groups are available on methotrexate, doxorubicin, daunorubicin, cytosinarabinoside, cis-platin, vindesine, mitomycin and bleomycin while free carboxylic acid groups are available on methotrexate, melphalan, and chlorambucil. These functional groups, that is free amino and carboxylic acids, are targets for a variety of homobifunctional and heterobifunctional chemical crosslinking agents which can crosslink these drugs directly to a free amino group of a PSMA ligand.

Peptide and polypeptide toxins are also useful as active moieties, and the present invention specifically contemplates embodiments wherein R is a toxin. Toxins are generally complex toxic products of various organisms including bacteria, plants, etc. Examples of toxins include but are not limited to: ricin, ricin A chain (ricin toxin), Pseudomonas exotoxin (PE), diphtheria toxin (DT), Clostridium perfringens phospholipase C (PLC), bovine pancreatic ribonuclease (1BPR), pokeweed antiviral protein (PAP), abrin, abrin A chain (abrin toxin), cobra venom factor (CVF), gelonin (GEL), saporin (SAP), modeccin, viscumin and volkensin.

In addition, there are other active agents which can be used to create a modified PSMA ligand for the treatment of cancer. For example, modified PSMA ligands can be generated to include active enzyme. The modified PSMA ligand specifically localizes the activity to the tumor cells. An inactive prodrug which can be converted by the enzyme into an active drug is administered to the patient. The prodrug is only converted to an active drug by the enzyme which is localized to the tumor. An example of an enzyme/prodrug pair includes alkaline phosphatase/etoposidephosphate. In such a case, the alkaline phosphatase is conjugated to a PSMA ligand. The modified PSMA ligand is administered and localizes at the metastasized cell. Upon contact with etoposidephosphate (the prodrug), the etoposidephosphate is converted to etoposide, a chemotherapeutic drug which is taken up by the cancer cell.

The present invention also contemplates dyes used, for example, in photodynamic therapy, and used in conjunction with appropriate non-ionizing radiation. The use of light and porphyrins in methods of the present invention is also contemplated and their use in cancer therapy has been reviewed, van den Bergh, Chemistry in Britain, 22: 430–437 (1986), which is incorporated herein in its entirety by reference.

The modified PSMA ligands of the invention can be, for example, formulated as a solution, suspension or emulsion in association with a pharmaceutically acceptable parenteral vehicle. Examples of such vehicles are water, saline, Ringer's solution, dextrose solution, and 5% human serum albumin. Liposomes may also be used. The vehicle may contain additives that maintain isotonicity (e.g., sodium chloride, mannitol) and chemical stability (e.g., buffers and preservatives). The formulation is sterilized by commonly used techniques. For example, a parenteral composition suitable for administration by injection is prepared by dissolving 1.5% by weight of active ingredient in 0.9% sodium chloride solution.

The pharmaceutical compositions according to the present invention may be administered as either a single dose or in multiple doses. The pharmaceutical compositions of the present invention may be administered either as individual therapeutic agents or in combination with other therapeutic agents. The treatments of the present invention may be combined with conventional therapies, which may be administered sequentially or simultaneously. The pharmaceutical compositions of the present invention may be administered by any means that enables the modified PSMA ligand to reach the targeted cells. In some embodiments, routes of administration include those selected from the group consisting of intravenous, intraarterial, intraperitoneal, local administration into the blood supply of the organ in which the tumor resides or directly into the tumor itself. Intravenous administration is the preferred mode of administration. It may be accomplished with the aid of an infusion pump.

The dosage administered varies depending upon factors such as: the nature of the active moiety, the nature of the modified PSMA ligand; pharmacodynamic characteristics; its mode and route of administration; age, health, and weight of the recipient; nature and extent of symptoms; kind of concurrent treatment; and frequency of treatment.

Because the subject ligands are specifically targeted to cells with PSMA/NAALADase activity, those modified PSMA ligands which comprise chemotherapeutics or toxins are administered in doses less than those which are used when the chemotherapeutics or toxins are administered as unconjugated active agents, preferably in doses that contain up to 100 times less active agent. In some embodiments, modified PSMA ligands which comprise chemotherapeutics or toxins are administered in doses that contain 10–100 times less active agent as an active moiety than the dosage of chemotherapeutics or toxins administered as unconjugated active agents. To determine the appropriate dose, the amount of compound is preferably measured in moles instead of by weight. In that way, the variable weight of different modified PSMA ligands does not affect the calculation. Presuming a one to one ratio of modified PSMA ligand to active moiety in modified PSMA ligands of the invention, less moles of modified PSMA ligands may be administered as compared to the moles of unmodified PSMA ligands administered, preferably up to 100 times less moles.

(iv) Exemplary Uses of the Subject Ligands

A. PSMA Ligands in Treatment of Disease Conditions

The present invention also relates to a method of treating a prostate disease in an animal, comprising administering an effective amount of a compound of formula I, II, III, IV or V to said animal. In a preferred embodiment, said prostate disease is prostate cancer such as prostatic adenocarcinoma, benign prostatic hyperplasia, or conditions involving the prostate requiring administration of the compounds of the present invention, such prostatic intraepithelial neoplasia (PIN).

In addition to prostate cancer, other forms of cancer that may be treated with the compounds of the present invention include without limitation: ACTH-producing tumors, acute lymphocytic leukemia, acute nonlymphocytic leukemia, cancer of the adrenal cortex, bladder cancer, brain cancer, breast cancer, cervix cancer, chronic lymphocytic leukemia, chronic myelocytic leukemia, colorectal cancer, cutaneous T-cell lymphoma, endometrial cancer, esophageal cancer, Ewing's sarcoma, gallbladder cancer, hairy cell leukemia, head & neck cancer, Hodgkin's lymphoma, Kaposi's sarcoma, kidney cancer, liver cancer, lung cancer(small and/or non-small cell), malignant peritoneal effusion, malignant pleural effusion, melanoma, mesothelioma, multiple myeloma, neuroblastoma, non-Hodgkin's lymphoma, osteosarcoma, ovary cancer, ovary (germ cell) cancer, pancreatic cancer, penis cancer, retinoblastoma, skin cancer, soft-tissue sarcoma, squamous cell carcinomas, stomach cancer, testicular cancer, thyroid cancer, trophoblastic neoplasms, cancer of the uterus, vaginal cancer, cancer of the vulva and Wilm's tumor.

The compounds of the present invention are particularly useful in treating cancer of tissues where PSMA/NAALADase enzymes reside. Such tissues include the prostate as well as the brain, kidney and testis.

For patients who initially present without advanced or metastatic cancer, the subject PSMA ligand-based drugs are used as an immediate initial therapy prior to surgery and radiation therapy, and as a continuous post-treatment therapy in patients at risk for recurrence or metastasis (based upon high PSMA, high Gleason's score, locally extensive disease, and/or pathological evidence of tumor invasion in the surgical specimen). The goal in these patients is to inhibit the growth of potentially metastatic cells from the primary tumor during surgery or radiotherapy and inhibit the growth of tumor cells from undetectable residual primary tumor.

For patients who initially present with advanced or metastatic cancer, PSMA ligand-based drugs are used as a continuous supplement to, or possible as a replacement for hormonal ablation. The goal in these patients is to slow tumor cell growth from both the untreated primary tumor and from the existing metastatic lesions.

In addition, the invention may be particularly efficacious during post-surgical recovery, where the present compositions and methods may be particularly effective in lessening the chances of recurrence of a tumor engendered by shed cells that cannot be removed by surgical intervention.

The present invention also includes a diagnostic kit for performing the methods of the present invention and may contain compounds and/or compositions containing the compounds of the present invention. For instance, radiolabeled ligands may be used in a manner so as to provide diagnostic information. Examples of diagnostic information and uses include determining the type of disease, the progress of the particular disease, the location of cells targeted by the modified PSMA ligand and similar diagnostic uses known to persons skilled in the art.

In the methods of the present invention, the compounds may be administered orally, parenterally, by inhalation spray, topically, rectally, nasally, buccally, vaginally or via an implanted reservoir in dosage formulations containing conventional non-toxic pharmaceutically-acceptable carriers, adjuvants and vehicles. The term parenteral as used herein includes subcutaneous, intravenous, intramuscular, intraperitoneal, intrathecal, intraventricular, intrasternal or intracranial injection and infusion techniques. Invasive techniques are preferred, particularly direct administration to damaged neuronal tissue.

To be effective therapeutically as central nervous system targets, the compounds of the present invention should readily penetrate the blood-brain barrier when peripherally administered. Compounds which cannot penetrate the blood-brain barrier can be effectively administered by an intraventricular route.

The compounds may also be administered in the form of sterile injectable preparations, for example, as sterile injectable aqueous or oleaginous suspensions. These suspensions can be formulated according to techniques known in the art using suitable dispersing or wetting agents and suspending agents. The sterile injectable preparations may also be sterile injectable solutions or suspensions in non-toxic parenterally- acceptable diluents or solvents, for example, as solutions in 1,3-butanediol. Among the acceptable vehicles and solvents that may be employed are water, Ringer's solution and isotonic sodium chloride solution. In addition, sterile fixed oils are conventionally employed as solvents or suspending mediums. For this purpose, any bland fixed oil such as a synthetic mono- or di-glyceride may be employed. Fatty acids such as oleic acid and its glyceride derivatives, including olive oil and castor oil, especially in their polyoxyethylated forms, are useful in the preparation of injectables. These oil solutions or suspensions may also contain long-chain alcohol diluents or dispersants.

Additionally, the compounds may be administered orally in the form of capsules, tablets, aqueous suspensions or solutions. Tablets may contain carriers such as lactose and corn starch, and/or lubricating agents such as magnesium stearate. Capsules may contain diluents including lactose and dried corn starch. Aqueous suspensions may contain emulsifying and suspending agents combined with the active ingredient. The oral dosage forms may further contain sweetening and/or flavoring and/or coloring agents.

The compounds may further be administered rectally in the form of suppositories. These compositions can be prepared by mixing the drug with suitable non-irritating excipients which are solid at room temperature, but liquid at rectal temperature such that they will melt in the rectum to release the drug. Such excipients include cocoa butter, beeswax and polyethylene glycols.

Moreover, the compounds may be administered topically, especially when the conditions addressed for treatment involve areas or organs readily accessible by topical application, including neurological disorders of the eye, the skin or the lower intestinal tract.

For topical application to the eye, or ophthalmic use, the compounds can be formulated as micronized suspensions in isotonic, pH adjusted sterile saline or, preferably, as a solution in isotonic, pH adjusted sterile saline, either with or without a preservative such as benzylalkonium chloride. Alternatively, the compounds may be formulated into ointments, such as petrolatum.

For topical application to the skin, the compounds can be formulated into suitable ointments containing the compounds suspended or dissolved in, for example, mixtures with one or more of the following: mineral oil, liquid petrolatum, white petrolatum, propylene glycol, polyoxyethylene polyoxypropylene compound, emulsifying wax and water. Alternatively, the compounds can be formulated into suitable lotions or creams containing the active compound suspended or dissolved in, for example, a mixture of one or more of the following: mineral oil, sorbitan monostearate, polysorbate 60, cetyl ester wax, cetearyl alcohol, 2-octyldodecanol, benzyl alcohol and water.

Topical application to the lower intestinal tract can be effected in rectal suppository formulations (see above) or in suitable enema formulations.

The compounds of the present invention may be administered by a single dose, multiple discrete doses or continuous infusion. Since the compounds are small, easily diffusible and relatively stable, they are well suited to continuous infusion. Pump means, particularly subcutaneous pump means, are preferred for continuous infusion.

Compositions and methods of the invention also may utilize controlled release technology. Thus, for example, modified PSMA ligands may be incorporated into a polymer matrix for controlled release over a period of days. Such controlled release films are well known to the art. Examples of polymers commonly employed for this purpose that may be used in the present invention include nondegradable ethylene-vinyl acetate copolymer and degradable lactic acid-glycolic acid copolymers. Certain hydrogels such as poly(hydroxyethylmethacrylate) or poly(vinylalcohol) also may be useful.

Dose levels on the order of about 0.1 mg to about 10,000 mg of the active ingredient compound are useful in the treatment of the above conditions, with preferred levels being about 0.1 mg to about 1,000 mg. The specific dose level for any particular patient will vary depending upon a variety of factors, including the activity of the specific compound employed; the age, body weight, general health, sex and diet of the patient; the time of administration; the rate of excretion; drug combination; the severity of the particular disease being treated; and the form of administration. Typically, in vitro dosage-effect results provide useful guidance on the proper doses for patient administration. Studies in animal models are also helpful, particularly in determining effective doses for treating cancer. The considerations for determining the proper dose levels are well known in the art.

For the methods of the present invention, any administration regimen regulating the timing and sequence of drug delivery can be used and repeated as necessary to effect treatment. Such regimen may include pretreatment and/or co-administration with additional therapeutic agents.

For patients with prostate cancer that is neither advanced nor metastatic, the compounds of the present invention may be administered (i) prior to surgery or radiation treatment to reduce the risk of metastasis; (ii) during surgery or in conjunction with radiation treatment; and/or (iii) after surgery or radiation therapy to reduce the risk of recurrence and to inhibit the growth of any residual tumorous cells.

For patients with advanced or metastatic prostate cancer, the compounds of the present invention may be administered as a continuous supplement to, or as a replacement for, hormonal ablation in order to slow tumor cell growth in both the untreated primary tumor and the existing metastatic lesions.

The methods of the present invention are particularly useful where shed cells could not be removed by surgical intervention. After post-surgical recovery, the methods of the present invention would be effective in reducing the chances of recurrence of a tumor engendered by such shed cells.

The modified PSMA ligands of the instant invention can also be used to determine the abundance of PSMA in a sample, based on their ability to bind PSMA. For example, the sample containing PSMA may be incubated with one of the modified PSMA ligands of the instant invention to allow binding between PSMA and its modified ligand. Bound ligands can then be separated from unbound ones, and the abundance of the bound PSMA ligands can be determined conveniently, especially when the abundance of the modifying group (the "R Group") is to be measured. The amount of bound modified PSMA ligands is partly determined by the binding affinity between the ligand and PSMA, it is also determined by the amount of PSMA in the sample. The relative amount of PSMA within different samples can be compared directly. However, when an absolute amount of PSMA within a sample is desired, a series of control samples with known PSMA concentrations can be employed to derive a standard curve, from which the absolute concentration of PSMA can be deduced.

There are many ways to determine the abundance of bound PSMA ligands. For example, if the modifying group is a fluorescent tag, the amount of fluorescent signals is a measurement of the ligand abundance. Similarly, the amount of chelate groups can be determined by the amount of radio-isotopes that can be bound by the chelate groups. Other embodiments of the invention will be apparent to skilled artisans.

Separation of bound and unbound PSMA ligands can be achieved in many conceivable ways. For example, PSMA within a test sample can be fixed on a solid support, such as in a well of a microtiter plate. Excessive unbound PSMA ligands, just like in an ELISA assay, can then be washed away. Alternatively, soluble PSMA can be immunoprecipitated using a PSMA-specific antibody, and the amount of the associated PSMA ligands determined using the methods described before.

B. Combination with Other Treatments (i) Surgery and Radiation Treatment

In general, surgery and radiation treatment are employed as potentially curative therapies for patients with localized prostate cancer who are under 70 years of age and are expected to live at least 10 more years.

Approximately 70% of newly diagnosed prostate cancer patients fall into this category. Approximately 90% of these patients (65% of total patients) undergo surgery, while approximately 10% of these patients (7% of total patients) undergo radiation treatment.

Histopathological examination of surgical specimens reveals that approximately 63% of patients undergoing surgery (40% of total patients) have locally extensive tumors or regional (lymph node) metastasis that was undetected at initial diagnosis. These patients are at a significantly greater risk of recurrence. Approximately 40% of these patients will actually develop recurrence within five years after surgery. Results after radiation treatment are even less encouraging. Approximately 80% of patients who have undergone radiation treatment as their primary therapy have disease persistence or develop recurrence or metastasis within five years after treatment.

Currently, most prostate cancer patients undergoing surgery and radiation treatment do not receive any immediate follow-up therapy. Rather, they are monitored frequently for elevated PSMA, which is the primary indicator of recurrence or metastasis.

Based on the above statistics, there is considerable opportunity to use the present invention in conjunction with surgery and/or radiation treatment.

(ii) Hormonal Therapy

Hormonal ablation is the most effective palliative treatment for the 10% of patients with metastatic prostate cancer. Hormonal ablation by medication and/or orchiectomy is used to block hormones that promote further growth and metastasis of prostate cancer. With time, both the primary and metastatic tumors of virtually all of these patients become hormone-independent and resistant to therapy. Approximately 50% of patients with metastatic cancer die within three years after initial diagnosis, and 75% of such patients die within five years after diagnosis. Continuous supplementation with the compounds of the present invention may be used to prevent or reverse this potentially metastasis-permissive state.

(iii) Chemotherapy

While chemotherapy has been successful in treating some forms of cancer, it has shown slight therapeutic value in treating prostate cancer where it is generally reserved as a last resort. Accordingly, the opportunity to treat prostate cancer by combining chemotherapy with the methods of the present invention will be rare. When combined, however, such treatments should be more effective than chemotherapy alone in controlling prostate cancer.

(iv) Immunotherapy

The compounds of the present invention may also be used in combination with monoclonal antibodies to treat prostate cancer. Such combined treatment is particularly effective for patients with pelvic lymph node involvement, of which only 34% survive after 5 years. An example of such monoclonal antibodies is cell membrane-specific anti-prostate antibody.

The present invention may also be used with immunotherapies based on polyclonal or monoclonal antibody-derived reagents. Monoclonal antibody-derived reagents are preferred. These reagents are well known in the art, and include radiolabeled monoclonal antibodies such as monoclonal antibodies conjugated with strontium-89.

(v) Cryotherapy

The methods of the present invention may also be used in conjunction with cryotherapy for treatment of prostate cancer.

(vi) Chemical Prostatectomy

The methods and compositions of the invention may also be used for chemical ablation of the prostate gland, or "chemical prostatectomy." Chemical prostatectomy may be used as a non-surgical means of treatment for an individual with a diseased prostate. Alternatively, such a method may be used as a preventive treatment for individuals at high risk of developing a prostate associated disease or disorder, e.g., individuals with a positive family history or personal history of prostate disease.

Exemplification

The invention now being generally described, it will be more readily understood by reference to the following examples which are included merely for purposes of illustration of certain aspects and embodiments of the present invention, and are not intended to limit the scope of the invention.

EXAMPLE 1

Conjugation of Guilford 11254-36 to the Near-Infrared Fluorophore IRDye78

To demonstrate that PSMA ligands can be functionalized according to the instant invention, compound Guilford 11254-36 was conjugated under aqueous conditions to the near-infrared fluorophore IRDye78 (LI-COR, Lincoln, Nebr.; excitation 771 nm, emission 796 nm) using the chemistry shown in FIG. 1A IRDye78 is a near-infrared fluorophore that can be used in the intraoperative detection of cancer cells in a surgical field.

The desired product of the reaction could be easily separated from reactants using normal phase thin-layer chromatography (FIG. 1B). A skilled artisan would be able to utilize other commonly known techniques to isolate, or purify the conjugated chemical product.

EXAMPLE 2

Near-Infrared Fluorescent Detection of PSMA in Living Cells using a Functionalized PSMA Ligand To demonstrate that the compound of the instant invention (functionalized PSMA ligand) still retains the ability to bind PSMA, just like the unconjugated PSMA ligand, the compound Guilford 11254-36 was conjugated to the near-infrared fluorophore IRDye78 as described above. COS-7 cells, which normally do not express PSMA, were infected with an adenovirus that either co-express GFP and PSMA (left column), or expresses GFP only (right column). 72 hours after infection, cells were incubated with 5 μM $CaCl_2$ for 15 minutes at 37° C. Cells were then washed 3× with PBS supplemented with 10 μM $MgCl_2$ and 1 μM $CaCl_2$ and viewed under a fluorescent microscope using various filter sets.

Figure 2:
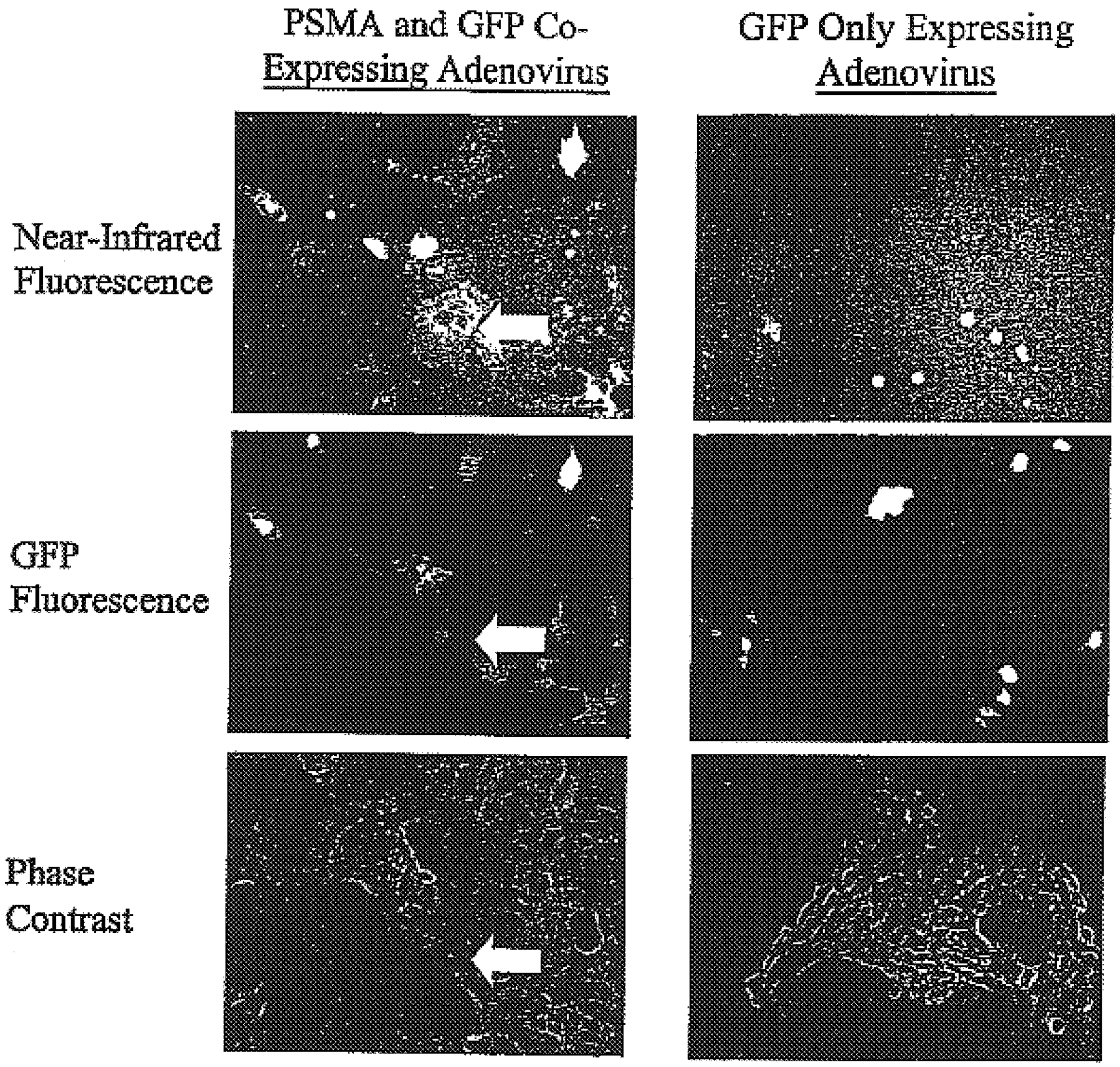
FIG. 2. COS-7 cells, which normally do not express PSMA, were infected by adenovirus constructs expressing GFP, or co-expressing GFP and PSMA. Top panel shows near-infrared fluorescence (excitation 771 nm, emission 796 nm). Middle panel shows green fluorescent protein signal. Bottom panel shows phase contrast of same field. Arrow points to representative cell with nuclear/cytoplasmic GFP signal and strong plasma membrane Guilford/IRDye78 signal. Control cells expressing GFP only (right column) do not bind Guilford/IRD78 conjugate.

FIG. 2 middle panels shows that COS-7 cells were infected efficiently by the adenovirus and many cells in the view field expressed the GFP marker (and presumably also the PSMA protein in the left column). Although there is no morphological differences between the GFP expressing and GFP-PSMA co-expression cells FIG. 2, bottom panels), it is clear that the functionalized PSMA ligand, IRDye78 conjugated to Guilford 11254-36, can bind GFP-PSMA co-expressing cells (FIG. 2, top panel, left column), as is evident from the near-infrared fluorescence (excitation 771 nm, emission 796 nm). The strong plasma membrane Guilford/IRDye78 signal demonstrate that the PSMA protein is correctly localized the its usual plasma membrane localization. In contrary, control GFP-expressing cells do not bind Guilford/IRD78 conjugate (FIG. 2, top panel, right column).

EXAMPLE 3

Proof of Specificity of the Modified PSMA Ligand

To demonstrate that the functionalized PSMA ligand retains the binding specificity to PSMA, COS-7 cells were infected with an adenovirus that either co-express GFP and PSMA (left column), or co-expresses GFP and Erb-B2 (a breast cancer protein; right column). 72 hours after transfection, cells were incubated with 5 μM of the Guilford/IRDye78 conjugate in PBS supplemented with 10 μM $MgCl_2$ and 1 μM $CaCl_2$ for 15 minutes at 37° C. Cells were then washed 3× with PBS supplemented with 10 μM $CaCl_2$, fixed in 2% paraformaldehyde for 10 minutes at room temperature, washed, and viewed under a fluorescent microscope using various filter sets.

Figure 3:
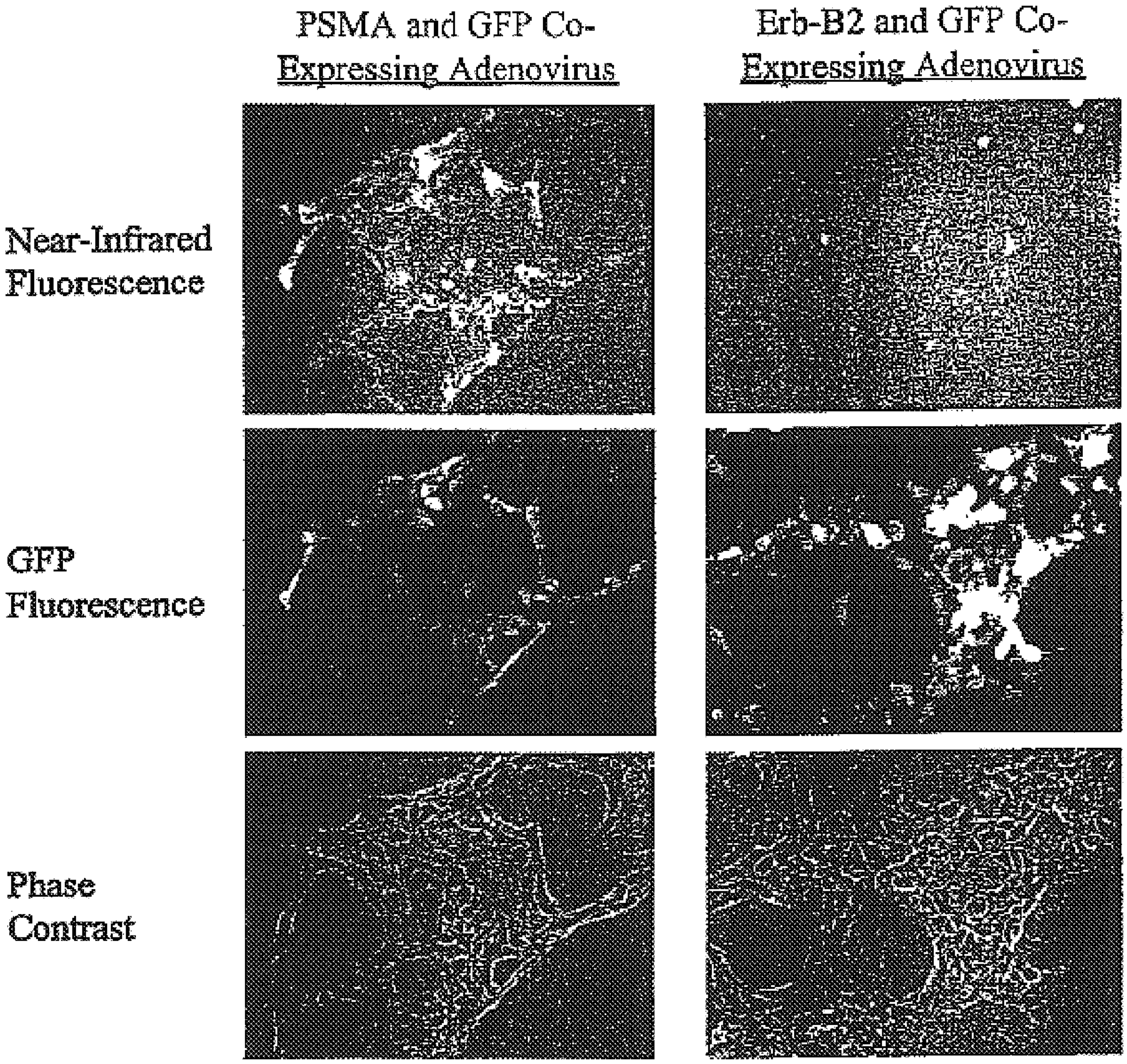
FIG. 3. COS-7 cells, which normally do not express PSMA, were infected by adenovirus constructs co-expressing GFP and cell surface protein Erb-b2, or co-expressing GFP and PSMA. Top panel shows near-infrared fluorescence (excitation 771 nm, emission 796 nm). Middle panel shows green fluorescent protein signal. Bottom panel shows phase contrast of same field. Arrow points to representative cell with strong plasma membrane Guilford/IRDye78 signal in cells making PSMA. No binding is seen with cells expressing Erb-B2 (right panel).

In FIG. 3, top panel shows near-infrared fluorescence (excitation 771 nm, emission 796 nm). Middle panel shows green fluorescent protein signal. Bottom panel shows phase contrast of same field. Arrow points to representative cell with strong plasma membrane Guilford/IRDye78 signal in cells making PSMA. No binding is seen with cells expressing Erb-B2 (right panel). This demonstrates that the functionalized PSMA ligand retains the binding specificity of the unconjugated PSMA ligand.

Figure 4:
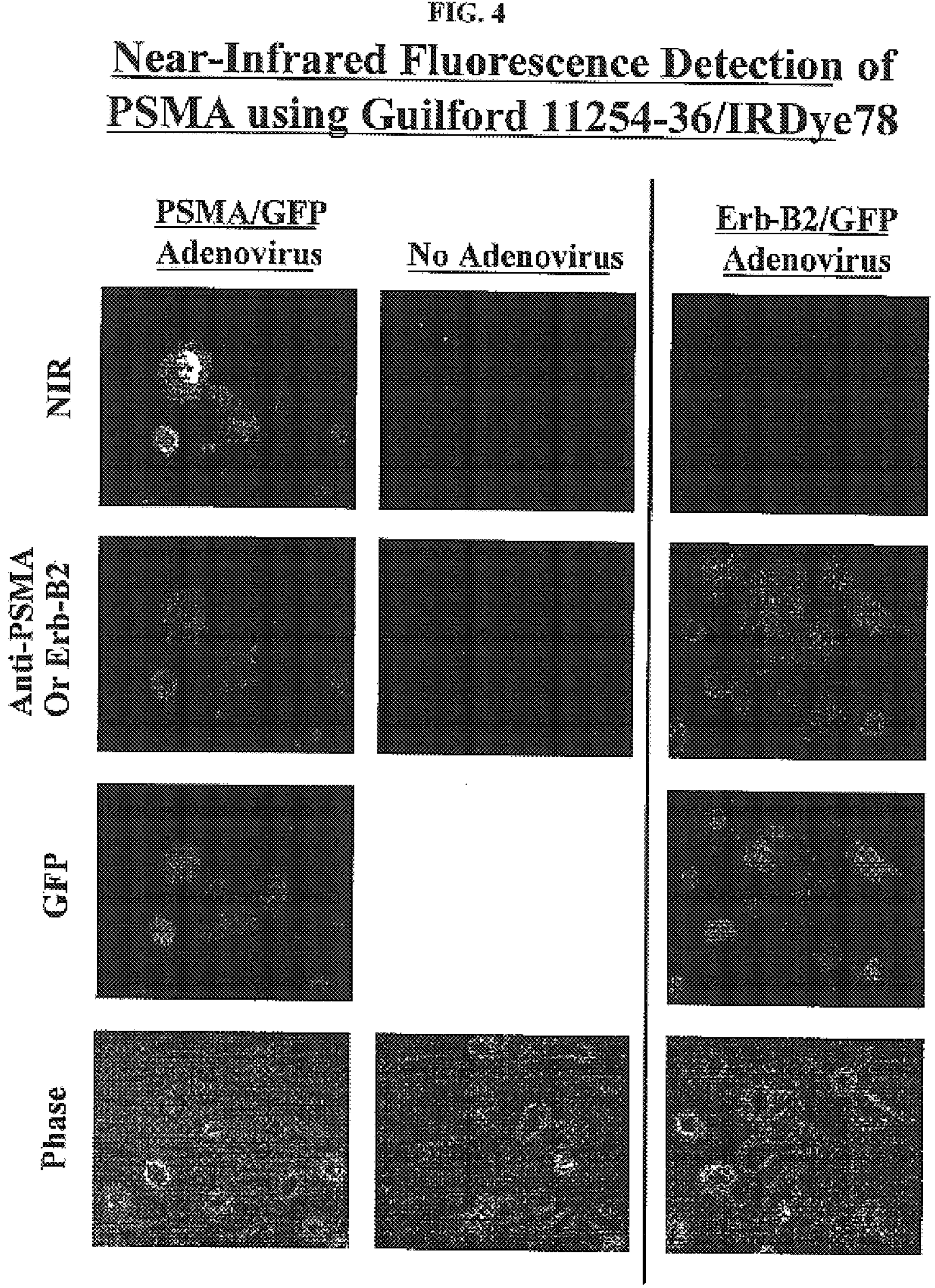
FIG. 4. PC-3 cells, a human prostate cancer cell line which normally do not express PSMA, were infected by adenovirus constructs co-expressing GFP and cell surface protein Erb-b2, or co-expressing GFP and PSMA. The middle column represents uninfected control PC-3 cells. The first row shows near-infrared fluorescence (excitation 771 nm, emission 796 rum). The second row shows immunostaining using either Erb-b2 or PSMA specific antibodies. The third row shows green fluorescent protein signal. The last row shows phase contrast of same field. Strong plasma membrane Guilford/IRDye78 signal is seen only in cells making PSMA. No binding is seen with cells expressing Erb-B2 (right panel) or control PC-3 cells.

Similar experiments have also been performed in a second cell-type, PC-3 cells, a human prostate cancer cell line which normally do not express PSMA. Essentially the same results were obtained as described above for COS-7 cells (FIG. 4).

EXAMPLE 4

PSMA Ligands and IRDye78 Inhibit PSMA Activity

To determine the effects of several PSMA ligands and modified PSMA ligands (β-AG/78) on PSMA activity, $^3$H-NAAG assay (Slusher et al., J. Biol. Chem., 1990, 265: 21297-301) was used to measure the activity of PSMA at the presence or absence of several PSMA ligands.

β-AG/78 (FIG. 5, bottom panel) is a conjugate of β-AG and the near-infrared fluorophore IRDye78. The conjugate can be synthesized using a similar scheme as shown in Example 1, and the product can be purified using either TLC (not shown) or HPLC, as shown in FIG. 6. As a control, IRDye78 was also tested. The results were shown as percentage of remaining PSMA activity as compared to PSMA activity without any additives, over a range of inhibitor concentrations.

Figure 5:
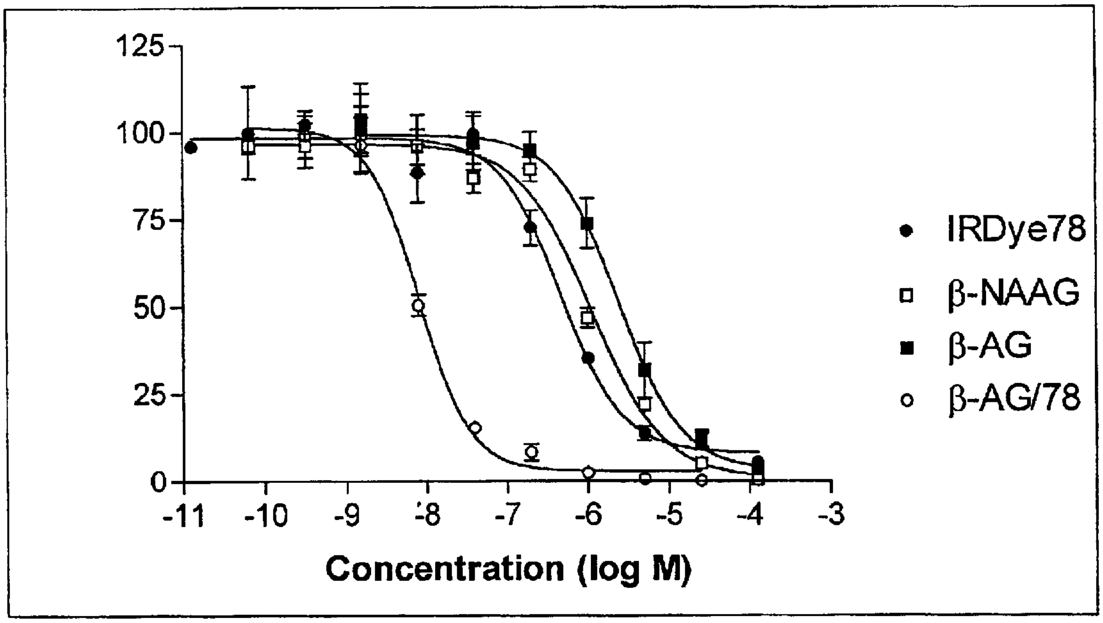
FIG. 5. Top panel: β-Asp-Glu (β-AG) is an inhibitor of PSMA enzymatic activity as measured by a $^3$H-NAAG assay. The vertical axis represents wild-type PSMA activity in percentage (100% represents full wild-type activity). The inhibitory activity of β-AG is compared to a PSMA competitive inhibitor beta-N-acetyl-AG (β-NAAG). Interestingly, IRDye78 is itself found to be a potent inhibitor of PSMA, and the conjugated β-AG/IRDye78 (β-AG/78) exhibits a synergistic inhibitory effect to PSMA when compared to either β-AG or unconjugated IRDye78. Bottom panel: structure of the conjugated β-AG/IRDye78 (β-AG/78).
Figure 5:
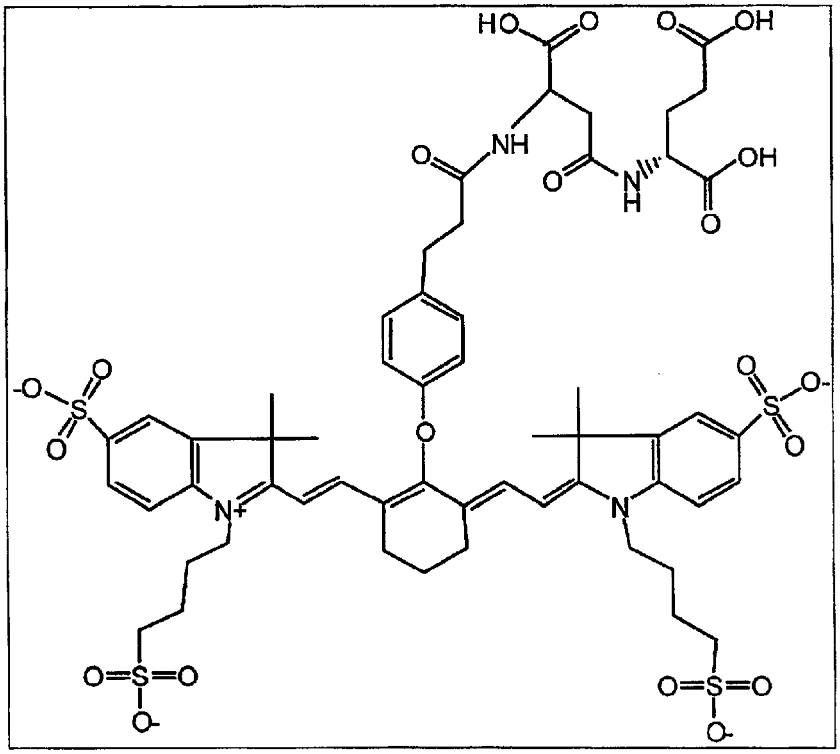
Figure 6:
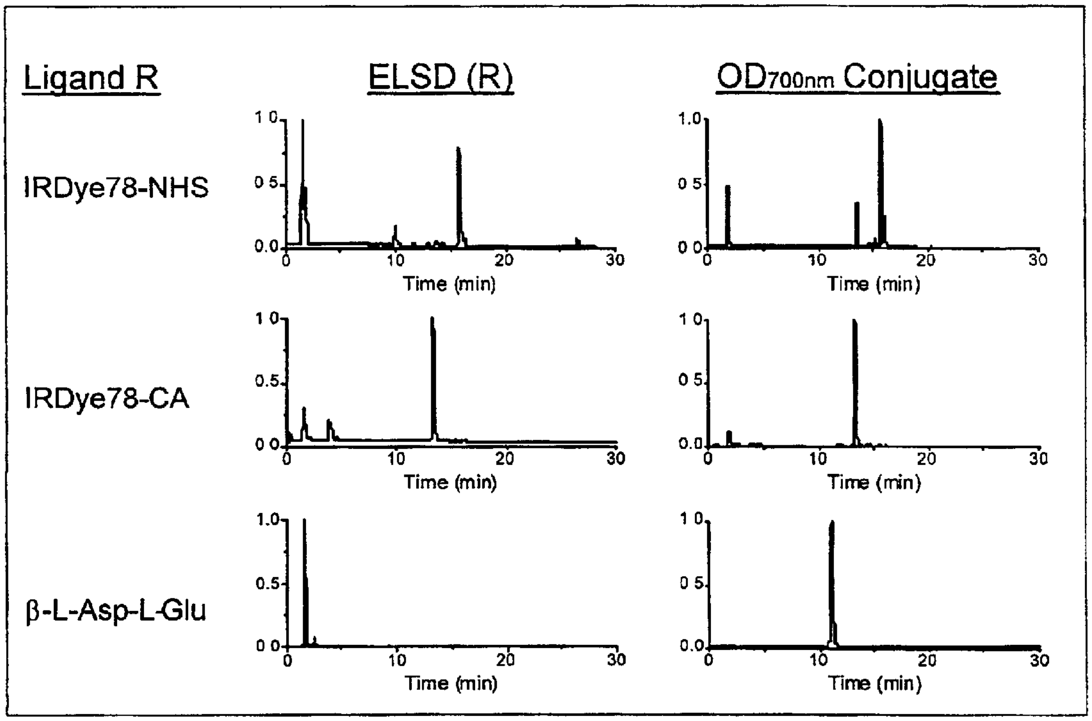
FIG. 6. Top panel: purification of β-AG/IRDye78 (β-AG/78) was accomplished by either TLC (not shown) or HPLC. Bottom panel: structure of β-AG.
Figure 6:
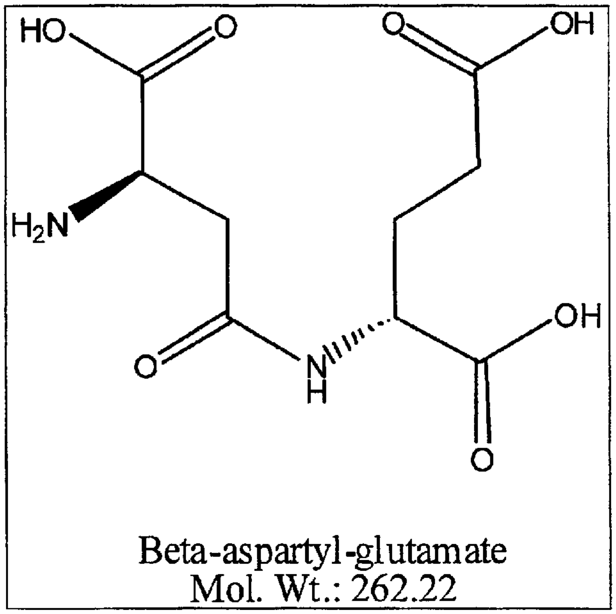

The result shown in FIG. 5, top panel, demonstrated that β-AG is indeed an inhibitor of PSMA enzymatic activity as measured by the $^3$H-NAAG assay. The inhibitory activity of β-AG was slightly less potent than that of beta-N-acetyl-AG (β-NAAG). Surprisingly, the IRDye78 is also an inhibitor of PSMA. In addition, the inhibitory effect of IRDye78 and β-AG are synergistic so that the β-AG/78 conjugate is a much more potent inhibitor than either β-AG or IRDye78 alone.

Figure 7:
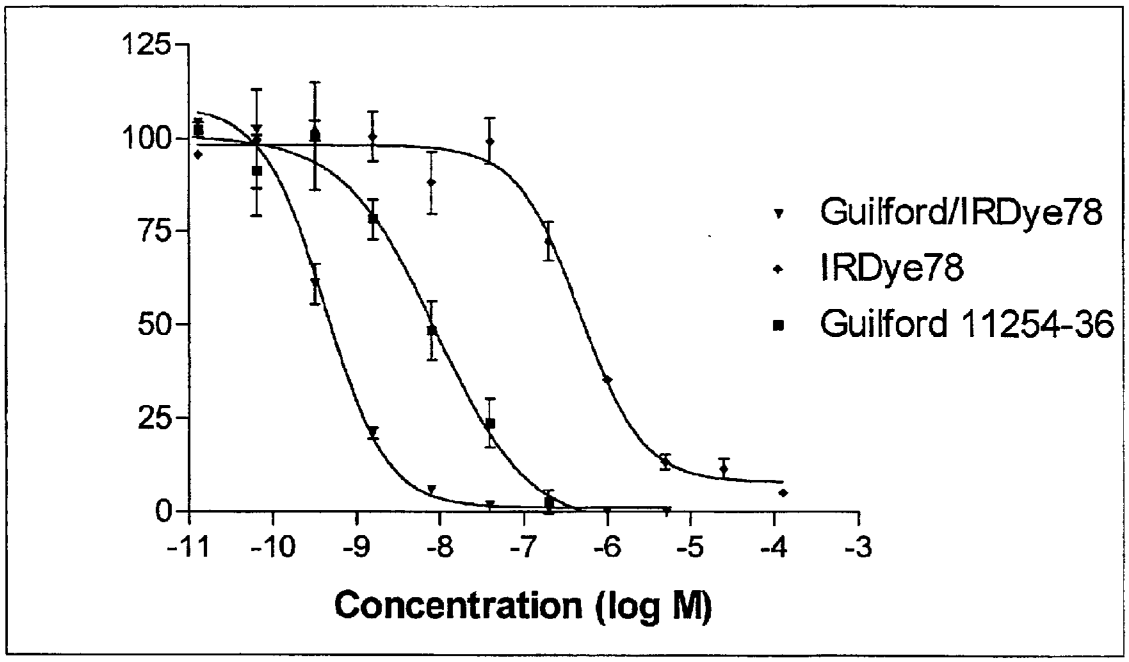
FIG. 7. Top panel: the Guilford/IRDye78 conjugate has a potency for PSMA inhibition that is synergistic with either compound alone. PSMA enzymatic activity is measured by a $^3$H-NAAG assay. The vertical axis represents wild-type PSMA activity in percentage (100% represents full wild-type activity). The inhibitory activity of Guilford/IRDye78 is compared to IRDye78 and Guilford 11254-36, the structure of which is shown in the lower panel.
Figure 7:
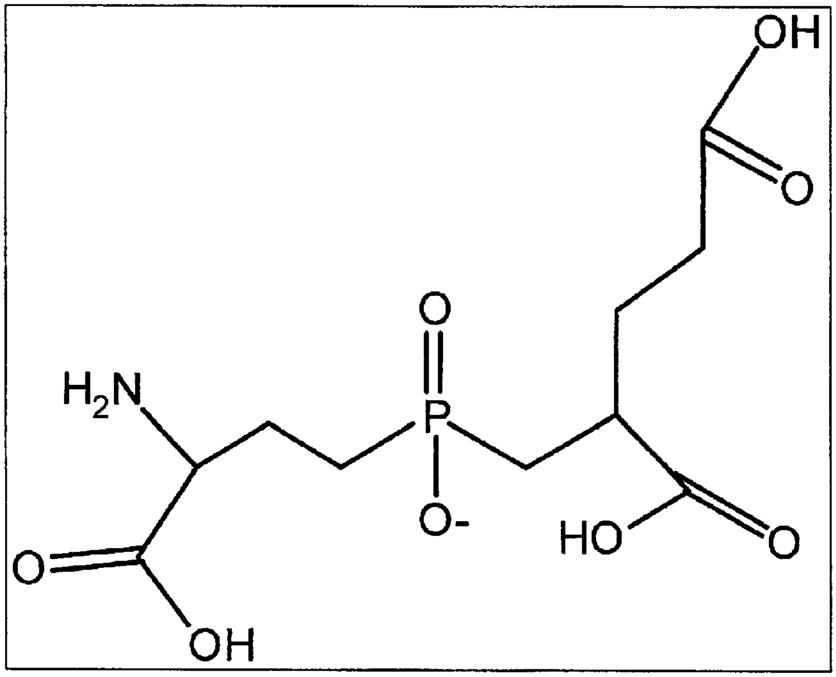

Similar results were obtained from a different set of experiments, where a Guilford 11254-36/IRDye78 conjugate (synthesis see Example 1) was found to be a more potent inhibitor than either Guilford 11254-36 (FIG. 7, bottom panel) or IRDye78 alone (FIG. 7, top panel), indicating that the inhibitory effects of IRDye78 and the Guilford compound are synergistic.

EXAMPLE 5

Modified PSMA Ligands Bind Directly to PSMA

Figure 8:
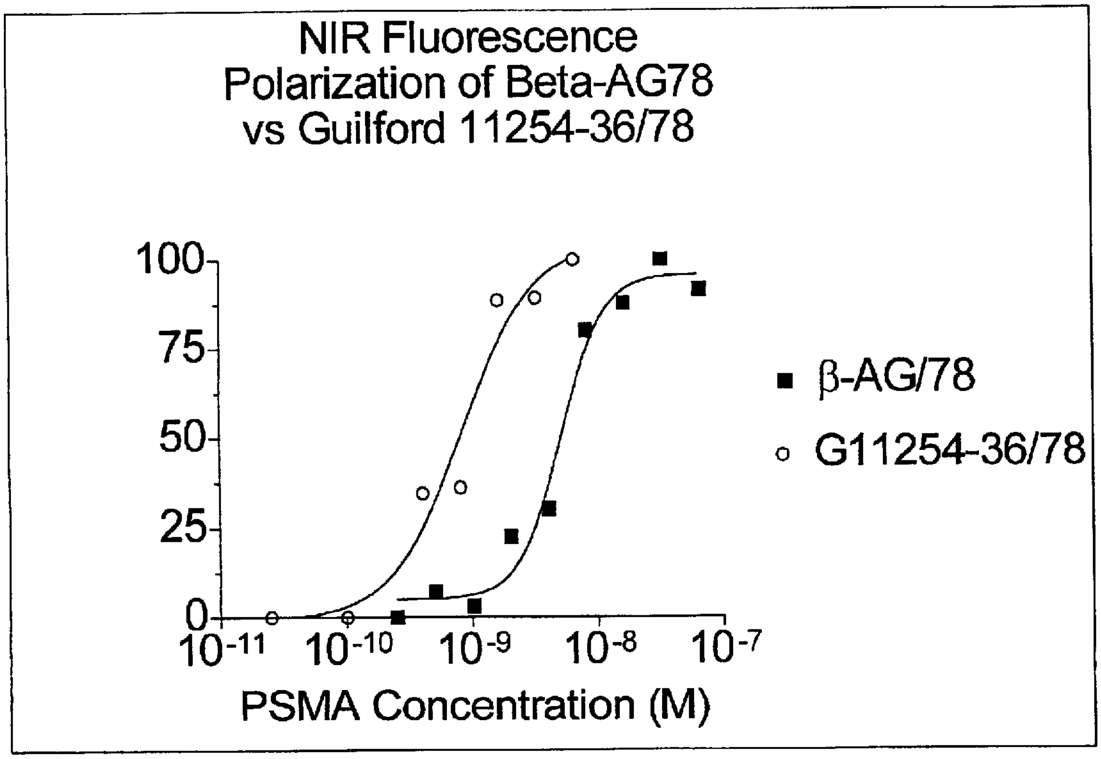
FIG. 8. The conjugates (beta-AG/78 and Guilford/78) created by conjugation to the primary amine not only inhibit activity, but can also be proven to bind directly to the PSMA molecule. As shown in the fluorescence polarization data, both beta-AG/78 and Guilford/78 binds directly to PSMA with a $K_d$ essentially equivalent to their respective $IC_{50}$ of enzyme inhibition. This means that $IC_{50}$ can be used as a surrogate for affinity, and also predicts that the conjugates presented herein can be used as visualization agents for PSMA-positive cells.

As shown in the fluorescence polarization data of FIG. 8, both beta-AG/78 and Guilford/78 binds directly to PSMA with a $K_d$ essentially equivalent to their respective $IC_{50}$'s of enzyme inhibition. This means that $IC_{50}$ can be used as a surrogate for affinity, and also predicts that the conjugates presented herein can be used as visualization agents for PSMA-positive cells. Indeed, this is shown to be the case in experiments conducted in both COS-7 cells and PC-3 cells (see Examples 2 and 3).

EXAMPLE 6

Serum Stability of the Modified PSMA Ligand

It was determined that Guilford/78 is stable for up to 1 hour when incubated at 37 C in human serum (not shown).

We are presently testing detection in vivo in mouse xenograft models of prostate cancer, using the conjugated PSMA ligands.

Equivalents

It should be understood that the detailed description and the specific examples while indicating preferred embodiments of the invention are given by way of illustration only, since various changes and modifications within the spirit and scope of the invention will become apparent to those skilled in the art from this detailed description.

The references cited hereinabove are all incorporated herein by reference.

What is claimed is:

1. A compound represented in the formula (II):

II

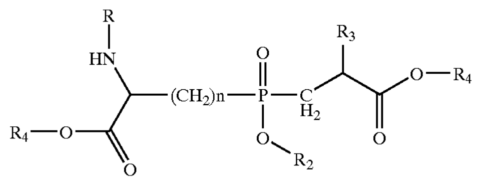

wherein:

R represents a chelate ligand, a fluorescence tag, or a cytotoxic moiety;

R3 represents an alkyl, an alkenyl, a cycloalkyl, a cycloalkenyl, an aryl, —$(CH_2)_m$-aryl, -alkyl-$CO_2$R4, -alkenyl-$CO_2$R4, -cycloalkyl-$CO_2$R4, -cycloalkenyl-$CO_2$R4 or -aryl-$CO_2$R4;

R2 and R4, independently for each occurrence, represent hydrogen, a lower alkyl, or a pharmaceutically acceptable salt;

m is 1, 2, 3 or 4; and, n is 0, 1, 2 or 3.

2. The compound of claim 1, wherein said cytotoxic moiety is a radiosensitizing agent, a Boron addend, a chemotherapeutic agent, a protein synthesis inhibitor, a prodrug activated by host metabolism, a cytotoxic toxin, an enzyme that converts prodrug locally, or a dye used in photodynamic therapy or in conjunction with appropriate non-ionizing radiation.

3. The compound of claim 1, wherein R is at least 25 amu in size.

4. The compound of claim 3, wherein R is at least 50 amu in size.

5. The compound of claim 4, wherein R is at least 100 amu in size.

6. The compound of claim 5, wherein R is at least 250 amu in size.

7. The compound of claim 1, wherein R is hydrolyzable from the PSMA ligand.

8. The compound of claim 7, wherein R is linked to the rest of the molecule by use of an amide or ester group.

9. The compound of claim 7, wherein R is linked to the rest of the molecule by use of an acid labile or base-cleavable linker.

10. The compound of claim 1, wherein R is a chelate moiety for chelating a metal.

11. The compound of claim 10, wherein R is a chelator for a radiometal or a paramagnetic ion.

12. The compound of claim 10, wherein R is a chelator for a radionuclide useful for radiotherapy or imaging procedures.

13. The compound of claim 12, wherein said radionuclide is a beta- or alpha-emitter for radio-therapeutic use.

14. The compound of claim 12, wherein said radionuclide is a gamma-emitter, positron-emitter, Auger electron-emitter, X-ray emitter or fluorescence-emitter.

15. The compound of claim 12, wherein said radionuclide is $^{99m}$Tc (technium).

16. The compound of claim 1, wherein R is a radiosensitizing agent selected from: nitroimidazoles, metronidazole or misonidazole.

17. The compound of claim 1, wherein R is a bifunctional chelator $N_xS_y$ that are capable of coordinately binding a metal or radiometal, wherein x and y are integers between 1 and 4.

18. The compound of claim 17, wherein $N_xS_y$ has a $N_2S_2$ or a $N_3S$ core.

19. The compound of claim 2, wherein said Boron addend is carborane.

20. The compound of claim 2, wherein said chemotherapeutic agent is: taxol; nitrogen mustards; ethylenimine derivatives; alkyl sulfonates; nitrosoureas; triazenes; pyrimidine analogs; purine analogs; vinca alkaloids; antibiotics; enzymes; platinum coordination complexes; substituted urea; methyl hydrazine derivatives; adrenocortical suppressants; or hormones and antagonists selected from: adrenocortisteroids (prednisone), progestins (hydroxyprogesterone caproate, medroprogesterone acetate and megestrol acetate), estrogens (diethylstilbestrol and ethinyl estradiol), antiestrogens (tamoxifen), or androgens (testosterone propionate and fluoxymesterone).

21. The compound of claim 2, wherein said protein synthesis inhibitor is puromycin, cycloheximide, or ribonuclease.

22. The compound of claim 2, wherein R is a prodrug that is only activated from its inactive precursor form by host metabolism.

23. The compound of claim 2, wherein said cytotoxic toxin is selected from: ricin, ricin A chain (ricin toxin), Pseudomonas exotoxin (PE), diphtheria toxin (DT), Clostridium perfringens phospholipase C (PLC), bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin or volkensin.

24. The compound of claim 2, wherein said enzyme that converts prodrug locally is alkaline phosphatase, and 'said prodrug is etoposidephosphate.

25. A pharmaceutical composition comprising the compound of claim 1, and a pharmaceutically acceptable carrier.

26. A method for detecting or imaging PSMA (prostate-specific membrane antigen)-expressing cells in a patient, comprising:

(a) contacting the patient with a modified PSMA ligand of claim 1;

(b) detecting the modified PSMA ligand, thereby detecting PSMA-expressing cells in the patient.

27. The method of claim 26, wherein the PSMA-expressing cells are prostatic cells in prostatic hyperplasia or prostate cancer.

28. The method of claim 26, wherein the modified PSMA ligand is modified by an imaging agent.

29. The method of claim 28, wherein the imaging agent is a radionuclide imaging agent.

30. The method of claim 29, wherein the radionuclide imaging agent is radioactive iodine or indium.

31. The method of claim 26, wherein the modified PSMA ligand is detected by radioscintigraphy, magnetic resonance imaging (MRI), computed tomography (CT scan), or positron emission tomography (PET).

32. The method of claim 26, wherein the contacting step (a) is effected by administering to the patient the modified PSMA ligand.

33. The method of claim 26, wherein the detecting step (b) includes determining the volume, shape and/or location of PSMA-expressing cells in the patient.

34. A method for determining the abundance of PSMA in a sample, comprising:

(a) contacting the sample with the modified PSMA ligands of claim 1;

(b) determining the abundance of the modified PSMA ligands bound to PSMA, or the abundance of the modifying group of said bound ligands, thereby determining the abundance of PSMA in said sample.

35. The method of claim 34, wherein the sample is prostatic fluid, urine, or obtained from seminal plasma.

36. A method to diagnose, in a test sample, the presence of a prostate disease condition associated with PSMA-overexpression, comprising:

(a) using the method of claim 34, determining the abundance of PSMA in the test sample and a normal control sample;

(b) comparing the level of abundance of PSMA in the test sample and the control sample;

wherein statistically significant higher levels of abundance of PSMA in the test sample indicates the presence of a prostate disease condition associated with PSMA-overexpression.

37. A method to treat a patient suffering from a disease condition associated with PSMA-overexpression, comprising administering to the patient an effective amount of modified PSMA ligand of claim 1.

38. The method of claim 37, wherein the disease condition is prostatic hyperplasia or prostate cancer.

39. The method of claim 37, wherein the modified PSMA ligand is modified by a cytotoxic agent.

40. The method of claim 37, wherein the modified PSMA ligand is modified by a radiometal chelating agent.

41. The method of claim 40, further comprising infusing into the patient an effective amount of chelator compounds.

42. The method of claim 41, wherein the chelator compound is EDTA or DTPA.

43. The method of claim 37, wherein the modified PSMA ligand is administered to the patient at a dose that contain 10–100 times less active agent as an active moiety than the dosage of agent administered as unconjugated active agents.

44. A kit for diagnosing or detecting the presence of a PSMA, comprising:

(a) at least one of the modified PSMA ligand of claim 1;

(b) an instruction.

45. The kit of claim 44, wherein the modified PSMA ligand contains a chelate moiety for chelating a metal or a paramagnetic ion.

46. The kit of claim 45, further comprising at least one metal.

47. The kit of claim 46, wherein the metal is a radionuclide useful for radiotherapy or imagine procedures.

* * * * *